US009856490B2

United States Patent
Verslues

(10) Patent No.: US 9,856,490 B2
(45) Date of Patent: Jan. 2, 2018

(54) DROUGHT-TOLERANT TRANSGENIC PLANT

(71) Applicant: Academia Sinica, Taipei (TW)

(72) Inventor: Paul Verslues, Taipei (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 14/865,689

(22) Filed: Sep. 25, 2015

(65) Prior Publication Data

US 2016/0090605 A1    Mar. 31, 2016

Related U.S. Application Data

(60) Provisional application No. 62/056,099, filed on Sep. 26, 2014.

(51) Int. Cl.
*C12N 15/82*    (2006.01)

(52) U.S. Cl.
CPC ..... *C12N 15/8273* (2013.01); *C12N 15/8218* (2013.01)

(58) Field of Classification Search
None
See application file for complete search history.

(56) References Cited

PUBLICATIONS

Whisstock J.C. et al. Prediction of protein function from protein sequence and structure. Q Rev Biophys. Aug. 2003;36(3):307-40. Review.*
Lu et al. AT14A mediates the cell wall-plasma membrane-cytoskeleton continuum in *Arabidopsis thaliana* cells. J Exp Bot. Jun. 2012;63(11):4061-9. Epub Mar. 28, 2012.*
Conti, et al., "Small Ubiquitin-like Modifier Protein SUMO Enables Plants to Control Growth Independently of the Phytohormone Gibberellin" Developmental Cell 28, 102-112, Jan. 13, 2014.
Lu, et al., "AT14A mediates the cell wall-plasma membrane-cytoskeleton continuum in *Arabidopsis thaliana* cells", Journal of Experimental Botany, vol. 63, No. 11, pp. 4061-4069, Mar. 2012.
Nagpal, et al., "Isolation and characterization of a cDNA clone from *Arabidopsis thaliana* with partial sequence similarity to integrins", Gene 230 (1999) 33-40.
Perella, et al., "Histone Deacetylase Complex1 Expression Level Titrates Plant Growth and Abscisic Acid Sensitivity in Arabidopsis C W OPEN", The plant Cell, vol. 25 ;3491-3505, Sep. 2013.
Reguera, et al., "Stress-Induced Cytokinin Synthesis Increases Drought Tolerance through the Coordinated Regulation of Carbon and Nitrogen Assimilation in Rice1 [C][W][Open]", Plant Physiology, Dec. 2013, vol. 169, pp. 1609-1622.
Rivero, et al., "Cytokinin-Dependent Photorespiration and the Protection of Photosynthesis during Water Deficit1[W][OA]", Plant Physiology, Jul. 2009, vol. 150, pp. 1530-1540.
Rivero, et al., "Delayed leaf senescence induces extreme drought tolerance in a flowering plant", PNAS, Dec. 4, 2007, vol. 104, No. 49, pp. 19631-19636.
Sardesai, et al., "Cytokinins Secreted by Agrobacterium Promote Transformation by Repressing a Plant Myb Transcription Factor", Plant Biology, Nov. 19, 2013, vol. 6, issue 302 pp. 1-11.
Skirycz, et al., "Survival and growth of Arabidopsis plants given limited water are not equal", Nature Biotechnology, vol. 29, No. 3, Mar. 2011 pp. 212-214.
Wang, et al., "Overexpression of AT14A confers tolerance to drought stress-induced oxidative damage in suspension cultured cells of *Arabidopsis thaliana*", Photoplasma (2015) 252:1111-1120.

\* cited by examiner

*Primary Examiner* — Cynthia Collins
(74) *Attorney, Agent, or Firm* — Cesari & McKenna LLP

(57) ABSTRACT

Described herein is a transgenic plant that comprises a recombinant DNA construct that contains a nucleic acid sequence operably linked to a promoter, the nucleic acid sequence encoding an AFL1 polypeptide, a recombinant DNA construct for inhibiting expression of a PD15 polypeptide or a NAI2 polypeptide, or a loss-of-function pdi5 or nai2 mutation, wherein the transgenic plant exhibits increased growth under drought as compared to a control plant.

16 Claims, 8 Drawing Sheets

SEQUENCE LISTING

```
<160> NUMBER OF SEQ ID NOS: 58

<210> SEQ ID NO 1
<211> LENGTH: 1125
<212> TYPE: DNA
<213> ORGANISM: Arabidopsis thaliana
<220> FEATURE:
<221> NAME/KEY: CDS
<222> LOCATION: (1)..(1125)
<220> FEATURE:
<221> NAME/KEY: gene
<222> LOCATION: (1)..(1125)
<223> OTHER INFORMATION: AFL1

<400> SEQUENCE: 1 atg gcg tta tcc aaa gat ttg atg ttg aaa tgc tcg gaa gac atg atg       48
Met Ala Leu Ser Lys Asp Leu Met Leu Lys Cys Ser Glu Asp Met Met
1               5                   10                  15 agt gct tac aaa tct gct tgt gaa gaa cac cca aaa cta aaa tcc ttt       96
Ser Ala Tyr Lys Ser Ala Cys Glu Glu His Pro Lys Leu Lys Ser Phe
                20                  25                  30 gat gct tcc ctt cag cag cga acc aac aaa atg ata gac tca ctc acc      144
Asp Ala Ser Leu Gln Gln Arg Thr Asn Lys Met Ile Asp Ser Leu Thr
```

```
                35                    40                    45
gtt gaa gac aag aat ggt tcg tcc tcc cca cac gac gca cac atg gag    192
Val Glu Asp Lys Asn Gly Ser Ser Ser Pro His Asp Ala His Met Glu
 50                  55                  60 ctc tcc aag cac cta gtt gaa gtt acc caa ggt gtg gca gac ttc att    240
Leu Ser Lys His Leu Val Glu Val Thr Gln Gly Val Ala Asp Phe Ile
 65                  70                  75                  80 acc gaa atc gaa gac gat gtg tgg gac aac caa gct cta aag tat ttg    288
Thr Glu Ile Glu Asp Asp Val Trp Asp Asn Gln Ala Leu Lys Tyr Leu
                     85                  90                  95 gtc ctg gcc tat ttt gaa aat act aaa aag act tta gag att ttc aaa    336
Val Leu Ala Tyr Phe Glu Asn Thr Lys Lys Thr Leu Glu Ile Phe Lys
            100                 105                 110 act ata gag aac tgc gtc gag aac gca gaa atg ggc caa ctt ctc att    384
Thr Ile Glu Asn Cys Val Glu Asn Ala Glu Met Gly Gln Leu Leu Ile
        115                 120                 125 cga gag gcc ttg gcc gag ttt gag aaa gag tcg gca gaa aaa gat gtt    432
Arg Glu Ala Leu Ala Glu Phe Glu Lys Glu Ser Ala Glu Lys Asp Val
130                 135                 140 ggt ggg aaa aag aag aag tat gaa aaa aca ttg gag gac ctc aag agt    480
Gly Gly Lys Lys Lys Lys Tyr Glu Lys Thr Leu Glu Asp Leu Lys Ser
145                 150                 155                 160 ttt aaa gag atg gga gat ccc ttt gac ggc aaa gtt ctc aca act cag    528
Phe Lys Glu Met Gly Asp Pro Phe Asp Gly Lys Val Leu Thr Thr Gln
                165                 170                 175 ttc gag cgg atc aaa aag cag caa gaa tcc ctt ctg gag gaa gtg agt    576
Phe Glu Arg Ile Lys Lys Gln Gln Glu Ser Leu Leu Glu Glu Val Ser
            180                 185                 190 gag act aga aaa aag att cag gac gaa att agt aat cta gag aaa aaa    624
Glu Thr Arg Lys Lys Ile Gln Asp Glu Ile Ser Asn Leu Glu Lys Lys
        195                 200                 205 act tta att acg aac gtg gtt ttc ggc gct gcg ttt gct att gtt gcg    672
Thr Leu Ile Thr Asn Val Val Phe Gly Ala Ala Phe Ala Ile Val Ala
210                 215                 220 gtt gca tcc ata gct cta att gca aca ggc gtg ggt gcg gct gcc ggc    720
Val Ala Ser Ile Ala Leu Ile Ala Thr Gly Val Gly Ala Ala Ala Gly
225                 230                 235                 240 ttt ggg gct cta gcc gca cca ctg ctt gcg gca gga tgg gct gga gtc    768
Phe Gly Ala Leu Ala Ala Pro Leu Leu Ala Ala Gly Trp Ala Gly Val
                245                 250                 255 tac act acc ttg gat aaa aag aag gat gct ctg aac aaa cag tta gaa    816
Tyr Thr Thr Leu Asp Lys Lys Lys Asp Ala Leu Asn Lys Gln Leu Glu
            260                 265                 270 ggt cta aag aaa gtg gaa gag ata gaa gaa tcg gtg gag aaa ggt ata    864
Gly Leu Lys Lys Val Glu Glu Ile Glu Glu Ser Val Glu Lys Gly Ile
        275                 280                 285 aaa acc aac gaa gaa gcg acg gag acc gta tcg att tta gtc gac ggg    912
Lys Thr Asn Glu Glu Ala Thr Glu Thr Val Ser Ile Leu Val Asp Gly
290                 295                 300 cta gaa gac cgt atc aaa aat atg ttg aaa ctt gta gat aat gct att    960
Leu Glu Asp Arg Ile Lys Asn Met Leu Lys Leu Val Asp Asn Ala Ile
305                 310                 315                 320 gac cat gaa gat aat gag gcg gcc acg aga att gtc cta act cag atc   1008
Asp His Glu Asp Asn Glu Ala Ala Thr Arg Ile Val Leu Thr Gln Ile
                325                 330                 335 agt aag aaa gta gag aaa tta aca aag aaa atc acg gag gtt ggt gaa   1056
Ser Lys Lys Val Glu Lys Leu Thr Lys Lys Ile Thr Glu Val Gly Glu
            340                 345                 350 agt gtg gaa gat cat agc aag ttg att gca aag gcc aga ctt caa gtt   1104
```

Ser Val Glu Asp His Ser Lys Leu Ile Ala Lys Ala Arg Leu Gln Val
        355                 360                 365 ctg caa aag atc aac cgt taa                                    1125
Leu Gln Lys Ile Asn Arg
    370

<210> SEQ ID NO 2
<211> LENGTH: 374
<212> TYPE: PRT
<213> ORGANISM: Arabidopsis thaliana

<400> SEQUENCE: 2

Met Ala Leu Ser Lys Asp Leu Met Leu Lys Cys Ser Glu Asp Met Met
1               5                   10                  15

Ser Ala Tyr Lys Ser Ala Cys Glu Glu His Pro Lys Leu Lys Ser Phe
            20                  25                  30

Asp Ala Ser Leu Gln Gln Arg Thr Asn Lys Met Ile Asp Ser Leu Thr
        35                  40                  45

Val Glu Asp Lys Asn Gly Ser Ser Pro His Asp Ala His Met Glu
    50                  55                  60

Leu Ser Lys His Leu Val Glu Val Thr Gln Gly Val Ala Asp Phe Ile
65                  70                  75                  80

Thr Glu Ile Glu Asp Asp Val Trp Asp Asn Gln Ala Leu Lys Tyr Leu
                85                  90                  95

Val Leu Ala Tyr Phe Glu Asn Thr Lys Lys Thr Leu Glu Ile Phe Lys
            100                 105                 110

Thr Ile Glu Asn Cys Val Glu Asn Ala Glu Met Gly Gln Leu Leu Ile
        115                 120                 125

Arg Glu Ala Leu Ala Glu Phe Glu Lys Glu Ser Ala Glu Lys Asp Val
130                 135                 140

Gly Gly Lys Lys Lys Lys Tyr Glu Lys Thr Leu Glu Asp Leu Lys Ser
145                 150                 155                 160

Phe Lys Glu Met Gly Asp Pro Phe Asp Gly Lys Val Leu Thr Thr Gln
                165                 170                 175

Phe Glu Arg Ile Lys Lys Gln Gln Glu Ser Leu Leu Glu Glu Val Ser
            180                 185                 190

Glu Thr Arg Lys Lys Ile Gln Asp Glu Ile Ser Asn Leu Glu Lys Lys
        195                 200                 205

Thr Leu Ile Thr Asn Val Val Phe Gly Ala Ala Phe Ala Ile Val Ala
    210                 215                 220

Val Ala Ser Ile Ala Leu Ile Ala Thr Gly Val Gly Ala Ala Ala Gly
225                 230                 235                 240

Phe Gly Ala Leu Ala Ala Pro Leu Leu Ala Ala Gly Trp Ala Gly Val
                245                 250                 255

Tyr Thr Thr Leu Asp Lys Lys Asp Ala Leu Asn Lys Gln Leu Glu
            260                 265                 270

Gly Leu Lys Lys Val Glu Glu Ile Glu Glu Ser Val Glu Lys Gly Ile
        275                 280                 285

Lys Thr Asn Glu Glu Ala Thr Glu Thr Val Ser Ile Leu Val Asp Gly
    290                 295                 300

Leu Glu Asp Arg Ile Lys Asn Met Leu Lys Leu Val Asp Asn Ala Ile
305                 310                 315                 320

Asp His Glu Asp Asn Glu Ala Ala Thr Arg Ile Val Leu Thr Gln Ile
                325                 330                 335

Ser Lys Lys Val Glu Lys Leu Thr Lys Lys Ile Thr Glu Val Gly Glu

```
                        340                 345                 350
    Ser Val Glu Asp His Ser Lys Leu Ile Ala Lys Ala Arg Leu Gln Val
                355                 360                 365

Leu Gln Lys Ile Asn Arg
            370

<210> SEQ ID NO 3
<211> LENGTH: 1464
<212> TYPE: DNA
<213> ORGANISM: Arabidopsis thaliana
<220> FEATURE:
<221> NAME/KEY: CDS
<222> LOCATION: (1)..(1464)
<220> FEATURE:
<221> NAME/KEY: gene
<222> LOCATION: (1)..(1464)
<223> OTHER INFORMATION: PDI5

<400> SEQUENCE: 3 atg gcg atg agg ggc ttc acg ttg ttt tcg atc ctt gtg ttg tct ttg        48
Met Ala Met Arg Gly Phe Thr Leu Phe Ser Ile Leu Val Leu Ser Leu
1               5                   10                  15 tgc gct tcg tct atc aga agc gaa gag acg gag acg aag gag ttc gtg        96
Cys Ala Ser Ser Ile Arg Ser Glu Glu Thr Glu Thr Lys Glu Phe Val
            20                  25                  30 ttg acc ttg gat cac act aac ttc acc gat acc atc aac aaa cac gat       144
Leu Thr Leu Asp His Thr Asn Phe Thr Asp Thr Ile Asn Lys His Asp
        35                  40                  45 ttc atc gtc gtc gag ttc tac gcc cca tgg tgt gga cac tgc aag cag       192
Phe Ile Val Val Glu Phe Tyr Ala Pro Trp Cys Gly His Cys Lys Gln
    50                  55                  60 ctt gct cct gag tat gag aag gct gcg tca gct ttg agc agt aac gtc       240
Leu Ala Pro Glu Tyr Glu Lys Ala Ala Ser Ala Leu Ser Ser Asn Val
65                  70                  75                  80 cca cca gtg gtt ctt gct aag att gat gcc agt gag gaa aca aac aga       288
Pro Pro Val Val Leu Ala Lys Ile Asp Ala Ser Glu Glu Thr Asn Arg
                85                  90                  95 gaa ttt gca act caa tac gag gtt cag ggt ttc cca aca atc aag att       336
Glu Phe Ala Thr Gln Tyr Glu Val Gln Gly Phe Pro Thr Ile Lys Ile
            100                 105                 110 ttc aga aac gga gga aag gct gtt caa gaa tac aac gga cct cgt gaa       384
Phe Arg Asn Gly Gly Lys Ala Val Gln Glu Tyr Asn Gly Pro Arg Glu
        115                 120                 125 gct gag ggt att gtt act tac ttg aag aaa caa agt gga cct gct tct       432
Ala Glu Gly Ile Val Thr Tyr Leu Lys Lys Gln Ser Gly Pro Ala Ser
    130                 135                 140 gct gaa att aag tca gct gat gat gct tct gag gtt gtt agt gac aag       480
Ala Glu Ile Lys Ser Ala Asp Asp Ala Ser Glu Val Val Ser Asp Lys
145                 150                 155                 160 aag gtt gtt gtg gtt ggg att ttc cct aaa cta tct ggc tcc gag ttt       528
Lys Val Val Val Val Gly Ile Phe Pro Lys Leu Ser Gly Ser Glu Phe
                165                 170                 175 gat tct ttc atg gcc att gct gag aaa ttg cgc tct gag tta gat ttc       576
Asp Ser Phe Met Ala Ile Ala Glu Lys Leu Arg Ser Glu Leu Asp Phe
            180                 185                 190 gca cat acc tcg gat gcc aag ctt ctt ccc cgt gga gag tca tct gta       624
Ala His Thr Ser Asp Ala Lys Leu Leu Pro Arg Gly Glu Ser Ser Val
        195                 200                 205 aca gga cct gtg gtc agg cta ttc aaa ccc ttt gat gaa caa ttt gtt       672
Thr Gly Pro Val Val Arg Leu Phe Lys Pro Phe Asp Glu Gln Phe Val
    210                 215                 220
```

```
gat tcc aag gat ttc gat ggt gaa gct ctg gag aaa ttt gtc aaa gaa    720
Asp Ser Lys Asp Phe Asp Gly Glu Ala Leu Glu Lys Phe Val Lys Glu
225                 230                 235                 240 tcc agc att cca ctt atc acc gtc ttt gac aaa gat cca aac aac cac    768
Ser Ser Ile Pro Leu Ile Thr Val Phe Asp Lys Asp Pro Asn Asn His
            245                 250                 255 cca tat gtt atc aag ttc ttt gaa agc act aat acc aag gcg atg ttg    816
Pro Tyr Val Ile Lys Phe Phe Glu Ser Thr Asn Thr Lys Ala Met Leu
        260                 265                 270 ttc att aac ttc act gga gaa gga gct gag tct ctt aaa tca aag tac    864
Phe Ile Asn Phe Thr Gly Glu Gly Ala Glu Ser Leu Lys Ser Lys Tyr
    275                 280                 285 cgt gaa gtt gct aca tcc aac aag gga cag ggt ctt agc ttc ctt cta    912
Arg Glu Val Ala Thr Ser Asn Lys Gly Gln Gly Leu Ser Phe Leu Leu
290                 295                 300 ggt gat gct gag aac agc caa ggt gca ttc cag tac ttt gga ctc gaa    960
Gly Asp Ala Glu Asn Ser Gln Gly Ala Phe Gln Tyr Phe Gly Leu Glu
305                 310                 315                 320 gag agc caa gtt cct ctc atc atc atc cag act gct gac gac aag aaa   1008
Glu Ser Gln Val Pro Leu Ile Ile Ile Gln Thr Ala Asp Asp Lys Lys
            325                 330                 335 tac ctg aaa aca aat gtt gag gtt gac cag att gaa tca tgg gtc aag   1056
Tyr Leu Lys Thr Asn Val Glu Val Asp Gln Ile Glu Ser Trp Val Lys
        340                 345                 350 gac ttc aag gat gga aaa att gct ccc cac aaa aaa tct caa cct atc   1104
Asp Phe Lys Asp Gly Lys Ile Ala Pro His Lys Lys Ser Gln Pro Ile
    355                 360                 365 cca gcc gaa aac aac gag cca gtg aag gtt gtt gtt tct gac agc ctt   1152
Pro Ala Glu Asn Asn Glu Pro Val Lys Val Val Val Ser Asp Ser Leu
370                 375                 380 gac gac att gtc tta aac tct gga aag aac gtt ttg ctt gaa ttc tat   1200
Asp Asp Ile Val Leu Asn Ser Gly Lys Asn Val Leu Leu Glu Phe Tyr
385                 390                 395                 400 gct cca tgg tgt gga cac tgc caa aag ctt gct cca atc ttg gac gaa   1248
Ala Pro Trp Cys Gly His Cys Gln Lys Leu Ala Pro Ile Leu Asp Glu
            405                 410                 415 gtt gct gtg tcg tac caa agc gac tca agt gta gtc atc gct aag cta   1296
Val Ala Val Ser Tyr Gln Ser Asp Ser Ser Val Val Ile Ala Lys Leu
        420                 425                 430 gat gca acc gca aac gac ttc cca aaa gat acc ttt gat gtg aag gga   1344
Asp Ala Thr Ala Asn Asp Phe Pro Lys Asp Thr Phe Asp Val Lys Gly
    435                 440                 445 ttc ccg acc att tac ttc aaa tca gcg agc gga aac gtt gtg gtt tac   1392
Phe Pro Thr Ile Tyr Phe Lys Ser Ala Ser Gly Asn Val Val Val Tyr
450                 455                 460 gaa gga gac aga cag aga gaa tct ctt tat cta ttc att agg ttt tta   1440
Glu Gly Asp Arg Gln Arg Glu Ser Leu Tyr Leu Phe Ile Arg Phe Leu
465                 470                 475                 480 tat gtg cac tct tca gaa caa taa                                   1464
Tyr Val His Ser Ser Glu Gln
                485

<210> SEQ ID NO 4
<211> LENGTH: 487
<212> TYPE: PRT
<213> ORGANISM: Arabidopsis thaliana

<400> SEQUENCE: 4

Met Ala Met Arg Gly Phe Thr Leu Phe Ser Ile Leu Val Leu Ser Leu
1               5                   10                  15
```

```
Cys Ala Ser Ser Ile Arg Ser Glu Glu Thr Glu Lys Glu Phe Val
            20                  25                  30

Leu Thr Leu Asp His Thr Asn Phe Thr Asp Thr Ile Asn Lys His Asp
        35                  40                  45

Phe Ile Val Val Glu Phe Tyr Ala Pro Trp Cys Gly His Cys Lys Gln
    50                  55                  60

Leu Ala Pro Glu Tyr Glu Lys Ala Ala Ser Ala Leu Ser Ser Asn Val
65                  70                  75                  80

Pro Pro Val Val Leu Ala Lys Ile Asp Ala Ser Glu Glu Thr Asn Arg
                85                  90                  95

Glu Phe Ala Thr Gln Tyr Glu Val Gln Gly Phe Pro Thr Ile Lys Ile
            100                 105                 110

Phe Arg Asn Gly Gly Lys Ala Val Gln Glu Tyr Asn Gly Pro Arg Glu
        115                 120                 125

Ala Glu Gly Ile Val Thr Tyr Leu Lys Lys Gln Ser Gly Pro Ala Ser
    130                 135                 140

Ala Glu Ile Lys Ser Ala Asp Asp Ala Ser Glu Val Val Ser Asp Lys
145                 150                 155                 160

Lys Val Val Val Gly Ile Phe Pro Lys Leu Ser Gly Ser Glu Phe
                165                 170                 175

Asp Ser Phe Met Ala Ile Ala Glu Lys Leu Arg Ser Glu Leu Asp Phe
            180                 185                 190

Ala His Thr Ser Asp Ala Lys Leu Leu Pro Arg Gly Glu Ser Ser Val
        195                 200                 205

Thr Gly Pro Val Val Arg Leu Phe Lys Pro Phe Asp Glu Gln Phe Val
210                 215                 220

Asp Ser Lys Asp Phe Asp Gly Glu Ala Leu Glu Lys Phe Val Lys Glu
225                 230                 235                 240

Ser Ser Ile Pro Leu Ile Thr Val Phe Asp Lys Asp Pro Asn Asn His
            245                 250                 255

Pro Tyr Val Ile Lys Phe Phe Glu Ser Thr Asn Thr Lys Ala Met Leu
        260                 265                 270

Phe Ile Asn Phe Thr Gly Glu Gly Ala Glu Ser Leu Lys Ser Lys Tyr
    275                 280                 285

Arg Glu Val Ala Thr Ser Asn Lys Gly Gln Gly Leu Ser Phe Leu Leu
290                 295                 300

Gly Asp Ala Glu Asn Ser Gln Gly Ala Phe Gln Tyr Phe Gly Leu Glu
305                 310                 315                 320

Glu Ser Gln Val Pro Leu Ile Ile Gln Thr Ala Asp Asp Lys Lys
            325                 330                 335

Tyr Leu Lys Thr Asn Val Glu Val Asp Gln Ile Glu Ser Trp Val Lys
        340                 345                 350

Asp Phe Lys Asp Gly Lys Ile Ala Pro His Lys Lys Ser Gln Pro Ile
    355                 360                 365

Pro Ala Glu Asn Asn Glu Pro Val Lys Val Val Ser Asp Ser Leu
370                 375                 380

Asp Asp Ile Val Leu Asn Ser Gly Lys Asn Val Leu Leu Glu Phe Tyr
385                 390                 395                 400

Ala Pro Trp Cys Gly His Cys Gln Lys Leu Ala Pro Ile Leu Asp Glu
            405                 410                 415

Val Ala Val Ser Tyr Gln Ser Asp Ser Ser Val Ile Ala Lys Leu
        420                 425                 430

Asp Ala Thr Ala Asn Asp Phe Pro Lys Asp Thr Phe Asp Val Lys Gly
```

```
                    435                 440                 445
        Phe Pro Thr Ile Tyr Phe Lys Ser Ala Ser Gly Asn Val Val Tyr
        450                 455                 460

Glu Gly Asp Arg Gln Arg Glu Ser Leu Tyr Leu Phe Ile Arg Phe Leu
        465                 470                 475                 480

Tyr Val His Ser Ser Glu Gln
                        485

<210> SEQ ID NO 5
<211> LENGTH: 2319
<212> TYPE: DNA
<213> ORGANISM: Arabidopsis thaliana
<220> FEATURE:
<221> NAME/KEY: CDS
<222> LOCATION: (1)..(2319)
<220> FEATURE:
<221> NAME/KEY: gene
<222> LOCATION: (1)..(2319)
<223> OTHER INFORMATION: NAI2

<400> SEQUENCE: 5 atg gga aca aag ttt tta gct ctg ggt ttg tct ctg tgt ctt gtt ctc       48
Met Gly Thr Lys Phe Leu Ala Leu Gly Leu Ser Leu Cys Leu Val Leu
1               5                   10                  15 tca agc ttc tat caa gtt tct tgc cag gat gaa gga act gga agt ttg       96
Ser Ser Phe Tyr Gln Val Ser Cys Gln Asp Glu Gly Thr Gly Ser Leu
                20                  25                  30 agt act tta gat cta att gag cat gaa tat caa act agt gtc aat tct      144
Ser Thr Leu Asp Leu Ile Glu His Glu Tyr Gln Thr Ser Val Asn Ser
            35                  40                  45 ctc caa ggc aat gaa gca gta gat caa act gag acc agt ggt cag aaa      192
Leu Gln Gly Asn Glu Ala Val Asp Gln Thr Glu Thr Ser Gly Gln Lys
        50                  55                  60 aac agt aca gtg tct gat aac aac act att tct ttg tct cta tct gaa      240
Asn Ser Thr Val Ser Asp Asn Asn Thr Ile Ser Leu Ser Leu Ser Glu
65                  70                  75                  80 gaa cct gca ttg gaa act ctt aaa gaa tct gtt gat aca tca gct gag      288
Glu Pro Ala Leu Glu Thr Leu Lys Glu Ser Val Asp Thr Ser Ala Glu
                85                  90                  95 tta gga gct gtt act gat gaa gtc gat aaa cct tca agt atg ttg gac      336
Leu Gly Ala Val Thr Asp Glu Val Asp Lys Pro Ser Ser Met Leu Asp
            100                 105                 110 cat att gaa ctt gag ttc gaa gca cat atc aat gaa ctt aaa gaa gct      384
His Ile Glu Leu Glu Phe Glu Ala His Ile Asn Glu Leu Lys Glu Ala
        115                 120                 125 gga tct gat ggt atc aac aaa gtt gag gaa tct aaa gat gat gaa gaa      432
Gly Ser Asp Gly Ile Asn Lys Val Glu Glu Ser Lys Asp Asp Glu Glu
    130                 135                 140 gct gca agg aga cat aaa atg ttg gaa gcc att gaa cgt gaa ttt gaa      480
Ala Ala Arg Arg His Lys Met Leu Glu Ala Ile Glu Arg Glu Phe Glu
145                 150                 155                 160 gct gct cat gct gga ttt gaa caa cta aag act gat gat tcc gcc caa      528
Ala Ala His Ala Gly Phe Glu Gln Leu Lys Thr Asp Asp Ser Ala Gln
                165                 170                 175 gga tta gat gat gaa caa tct gca aag aga caa agc atg ttg gac gag      576
Gly Leu Asp Asp Glu Gln Ser Ala Lys Arg Gln Ser Met Leu Asp Glu
            180                 185                 190 att gaa cgt gat ttt gaa gct gct aca aaa ggt ctt gag caa cta aag      624
Ile Glu Arg Asp Phe Glu Ala Ala Thr Lys Gly Leu Glu Gln Leu Lys
        195                 200                 205 gct gat gat tta act gga atc aac gat gaa gaa cac gct gca aag aga      672
Ala Asp Asp Leu Thr Gly Ile Asn Asp Glu Glu His Ala Ala Lys Arg
```

-continued

```
                Ala Asp Asp Leu Thr Gly Ile Asn Asp Glu Glu His Ala Ala Lys Arg
                    210             215                 220 caa aag atg ctt gaa gag atc gaa aga gag ttt gaa gaa gct aca aaa      720
Gln Lys Met Leu Glu Glu Ile Glu Arg Glu Phe Glu Glu Ala Thr Lys
225                 230                 235                 240 ggt ctt gaa gaa cta agg cat tct acc tca agc aca gat gat gaa gca      768
Gly Leu Glu Glu Leu Arg His Ser Thr Ser Ser Thr Asp Asp Glu Ala
                    245                 250                 255 caa tct gca aag aga cag aat atg cta gat gag atc gaa cgg gag ttt      816
Gln Ser Ala Lys Arg Gln Asn Met Leu Asp Glu Ile Glu Arg Glu Phe
                260                 265                 270 gaa gct gct aca agt ggt ctt aaa gag cta aag att aat gct cac act      864
Glu Ala Ala Thr Ser Gly Leu Lys Glu Leu Lys Ile Asn Ala His Thr
            275                 280                 285 gtc aaa gat gat gtt gat gat aaa gaa caa gat gcc aaa aga caa agt      912
Val Lys Asp Asp Val Asp Asp Lys Glu Gln Asp Ala Lys Arg Gln Ser
        290                 295                 300 atg cta gat gca att gaa cgt gag ttt gaa gcc gtt acc gag agt ttt      960
Met Leu Asp Ala Ile Glu Arg Glu Phe Glu Ala Val Thr Glu Ser Phe
305                 310                 315                 320 aaa caa ctt gaa gat atc gcc gat aac aaa gct gaa gga gac gac gaa     1008
Lys Gln Leu Glu Asp Ile Ala Asp Asn Lys Ala Glu Gly Asp Asp Glu
                    325                 330                 335 tct gca aag agg caa agt atg ttg gat gag att gaa cgt gaa ttt gaa     1056
Ser Ala Lys Arg Gln Ser Met Leu Asp Glu Ile Glu Arg Glu Phe Glu
                340                 345                 350 gct gct aca aat agt ctt aag caa cta aac ctt gac gat ttc agt gaa     1104
Ala Ala Thr Asn Ser Leu Lys Gln Leu Asn Leu Asp Asp Phe Ser Glu
            355                 360                 365 gga gat gac agt gca gaa tct gca agg aga aat agt atg ctt gaa gct     1152
Gly Asp Asp Ser Ala Glu Ser Ala Arg Arg Asn Ser Met Leu Glu Ala
        370                 375                 380 atc gaa cgc gag ttt gaa gct gct aca aaa ggt ctt gaa gag cta aag     1200
Ile Glu Arg Glu Phe Glu Ala Ala Thr Lys Gly Leu Glu Glu Leu Lys
385                 390                 395                 400 gct aat gat tca acc ggc gac aag gat gat gat gaa cac gtt gca agg     1248
Ala Asn Asp Ser Thr Gly Asp Lys Asp Asp Asp Glu His Val Ala Arg
                    405                 410                 415 aga aaa att atg ctt gaa gct att gaa cgc gag ttt gaa gcc gcg aca     1296
Arg Lys Ile Met Leu Glu Ala Ile Glu Arg Glu Phe Glu Ala Ala Thr
                420                 425                 430 aaa ggc ctt gaa gag tta aag aat gaa tca gaa caa gct gaa aac aag     1344
Lys Gly Leu Glu Glu Leu Lys Asn Glu Ser Glu Gln Ala Glu Asn Lys
            435                 440                 445 aga aac agt atg ttg gaa gca ttc gaa cgc gaa ttt gaa gct gct aca     1392
Arg Asn Ser Met Leu Glu Ala Phe Glu Arg Glu Phe Glu Ala Ala Thr
        450                 455                 460 aat gca aag gct aat gga gaa aac tct gca aag aat cca tca acc ata     1440
Asn Ala Lys Ala Asn Gly Glu Asn Ser Ala Lys Asn Pro Ser Thr Ile
465                 470                 475                 480 agt act aca gtg cag aaa tct tct ggc gga tac aat gct ggt tta gaa     1488
Ser Thr Thr Val Gln Lys Ser Ser Gly Gly Tyr Asn Ala Gly Leu Glu
                    485                 490                 495 ggt ctt cta aag cct gca gat ggt gta tgt ggt tgt ttc aac aag gat     1536
Gly Leu Leu Lys Pro Ala Asp Gly Val Cys Gly Cys Phe Asn Lys Asp
                500                 505                 510 aaa gat ggt ctt cag gca gac act gat tct tcg att aac ata gcg gag     1584
Lys Asp Gly Leu Gln Ala Asp Thr Asp Ser Ser Ile Asn Ile Ala Glu
            515                 520                 525
```

| | | | | | | | | | | | | | | | |
|---|---|---|---|---|---|---|---|---|---|---|---|---|---|---|---|
| ata | ctc | gca | gaa | gaa | tcc | aaa | tta | cag | ggc | tca | ggg | acc | tct | cgg | ctc | 1632 |
| Ile | Leu | Ala | Glu | Glu | Ser | Lys | Leu | Gln | Gly | Ser | Gly | Thr | Ser | Arg | Leu | |
| | 530 | | | | 535 | | | | | 540 | | | | | | |

| acc | aca | tca | ttg | aac | aat | ctt | gtt | gat | act | cat | aga | aaa | gaa | acg | tcc | 1680 |
|---|---|---|---|---|---|---|---|---|---|---|---|---|---|---|---|---|
| Thr | Thr | Ser | Leu | Asn | Asn | Leu | Val | Asp | Thr | His | Arg | Lys | Glu | Thr | Ser | |
| 545 | | | | | 550 | | | | | 555 | | | | | 560 | |

| tca | aag | gta | ggc | tca | gtc | ctt | ggc | tca | tct | tca | tca | gtt | act | tct | acc | 1728 |
|---|---|---|---|---|---|---|---|---|---|---|---|---|---|---|---|---|
| Ser | Lys | Val | Gly | Ser | Val | Leu | Gly | Ser | Ser | Ser | Ser | Val | Thr | Ser | Thr | |
| | | | | 565 | | | | | 570 | | | | | 575 | | |

| aca | agc | gaa | tca | gcg | gct | aca | tca | gag | agc | ata | gag | agc | tta | aag | caa | 1776 |
|---|---|---|---|---|---|---|---|---|---|---|---|---|---|---|---|---|
| Thr | Ser | Glu | Ser | Ala | Ala | Thr | Ser | Glu | Ser | Ile | Glu | Ser | Leu | Lys | Gln | |
| | | | 580 | | | | | 585 | | | | | 590 | | | |

| aca | cta | agg | aag | cta | cgc | ggt | cta | agc | gca | cgt | gat | ctc | gta | aac | cac | 1824 |
|---|---|---|---|---|---|---|---|---|---|---|---|---|---|---|---|---|
| Thr | Leu | Arg | Lys | Leu | Arg | Gly | Leu | Ser | Ala | Arg | Asp | Leu | Val | Asn | His | |
| | | 595 | | | | | 600 | | | | | 605 | | | | |

| ccg | aat | ttc | gat | gcg | att | ata | gca | gcc | ggt | aca | cgt | tac | gag | gta | ctc | 1872 |
|---|---|---|---|---|---|---|---|---|---|---|---|---|---|---|---|---|
| Pro | Asn | Phe | Asp | Ala | Ile | Ile | Ala | Ala | Gly | Thr | Arg | Tyr | Glu | Val | Leu | |
| | 610 | | | | | 615 | | | | | 620 | | | | | |

| agc | tca | gct | tct | att | ggt | tac | atc | tct | ttg | cta | gcc | aaa | tac | aaa | acc | 1920 |
|---|---|---|---|---|---|---|---|---|---|---|---|---|---|---|---|---|
| Ser | Ser | Ala | Ser | Ile | Gly | Tyr | Ile | Ser | Leu | Leu | Ala | Lys | Tyr | Lys | Thr | |
| 625 | | | | | 630 | | | | | 635 | | | | | 640 | |

| gtc | att | aaa | gaa | gga | ctc | gag | gct | tct | cag | aga | gtc | cag | att | gct | caa | 1968 |
|---|---|---|---|---|---|---|---|---|---|---|---|---|---|---|---|---|
| Val | Ile | Lys | Glu | Gly | Leu | Glu | Ala | Ser | Gln | Arg | Val | Gln | Ile | Ala | Gln | |
| | | | | 645 | | | | | 650 | | | | | 655 | | |

| acc | cga | gcc | aaa | ctg | cta | aaa | gaa | acc | gca | atg | gag | aag | cag | aga | acc | 2016 |
|---|---|---|---|---|---|---|---|---|---|---|---|---|---|---|---|---|
| Thr | Arg | Ala | Lys | Leu | Leu | Lys | Glu | Thr | Ala | Met | Glu | Lys | Gln | Arg | Thr | |
| | | | 660 | | | | | 665 | | | | | 670 | | | |

| gta | gac | tcg | gtt | ttc | gca | gca | gca | aag | acc | act | gct | caa | aga | gga | gac | 2064 |
|---|---|---|---|---|---|---|---|---|---|---|---|---|---|---|---|---|
| Val | Asp | Ser | Val | Phe | Ala | Ala | Ala | Lys | Thr | Thr | Ala | Gln | Arg | Gly | Asp | |
| | | 675 | | | | | 680 | | | | | 685 | | | | |

| gcg | ttg | cac | atc | aga | atc | gta | gcg | atc | aag | aaa | ctg | ttg | gca | aag | cta | 2112 |
|---|---|---|---|---|---|---|---|---|---|---|---|---|---|---|---|---|
| Ala | Leu | His | Ile | Arg | Ile | Val | Ala | Ile | Lys | Lys | Leu | Leu | Ala | Lys | Leu | |
| | 690 | | | | | 695 | | | | | 700 | | | | | |

| gaa | gca | gag | aaa | gtg | gac | gtt | gat | tca | aag | ttc | acc | tct | tta | acg | acg | 2160 |
|---|---|---|---|---|---|---|---|---|---|---|---|---|---|---|---|---|
| Glu | Ala | Glu | Lys | Val | Asp | Val | Asp | Ser | Lys | Phe | Thr | Ser | Leu | Thr | Thr | |
| 705 | | | | | 710 | | | | | 715 | | | | | 720 | |

| agt | ctg | tca | gag | ctt | ctc | aag | gag | gcg | tca | cag | gct | tac | gaa | gag | tat | 2208 |
|---|---|---|---|---|---|---|---|---|---|---|---|---|---|---|---|---|
| Ser | Leu | Ser | Glu | Leu | Leu | Lys | Glu | Ala | Ser | Gln | Ala | Tyr | Glu | Glu | Tyr | |
| | | | | 725 | | | | | 730 | | | | | 735 | | |

| cac | gag | gcg | gtg | cat | aag | gca | aag | gac | gag | caa | gcg | gct | gag | gaa | ttt | 2256 |
|---|---|---|---|---|---|---|---|---|---|---|---|---|---|---|---|---|
| His | Glu | Ala | Val | His | Lys | Ala | Lys | Asp | Glu | Gln | Ala | Ala | Glu | Glu | Phe | |
| | | | 740 | | | | | 745 | | | | | 750 | | | |

| gcg | gtg | gag | acg | aca | aag | aga | gca | gaa | cat | att | tgg | gtt | gag | ttt | ctt | 2304 |
|---|---|---|---|---|---|---|---|---|---|---|---|---|---|---|---|---|
| Ala | Val | Glu | Thr | Thr | Lys | Arg | Ala | Glu | His | Ile | Trp | Val | Glu | Phe | Leu | |
| | | 755 | | | | | 760 | | | | | 765 | | | | |

| agt | tca | ctt | aat | tga | | | | | | | | | | | | 2319 |
|---|---|---|---|---|---|---|---|---|---|---|---|---|---|---|---|---|
| Ser | Ser | Leu | Asn | | | | | | | | | | | | | |
| | 770 | | | | | | | | | | | | | | | |

<210> SEQ ID NO 6
<211> LENGTH: 772
<212> TYPE: PRT
<213> ORGANISM: Arabidopsis thaliana

<400> SEQUENCE: 6

Met Gly Thr Lys Phe Leu Ala Leu Gly Leu Ser Leu Cys Leu Val Leu
1               5                   10                  15

Ser Ser Phe Tyr Gln Val Ser Cys Gln Asp Glu Gly Thr Gly Ser Leu
            20                  25                  30

Ser Thr Leu Asp Leu Ile Glu His Glu Tyr Gln Thr Ser Val Asn Ser

```
                35                  40                  45
Leu Gln Gly Asn Glu Ala Val Asp Gln Thr Glu Thr Ser Gly Gln Lys
 50                  55                  60
Asn Ser Thr Val Ser Asp Asn Thr Ile Ser Leu Ser Leu Ser Glu
 65                  70                  75                  80
Glu Pro Ala Leu Glu Thr Leu Lys Glu Ser Val Asp Thr Ser Ala Glu
                 85                  90                  95
Leu Gly Ala Val Thr Asp Glu Val Asp Lys Pro Ser Ser Met Leu Asp
                100                 105                 110
His Ile Glu Leu Glu Phe Glu Ala His Ile Asn Glu Leu Lys Glu Ala
                115                 120                 125
Gly Ser Asp Gly Ile Asn Lys Val Glu Glu Ser Lys Asp Asp Glu Glu
                130                 135                 140
Ala Ala Arg Arg His Lys Met Leu Glu Ala Ile Glu Arg Glu Phe Glu
145                 150                 155                 160
Ala Ala His Ala Gly Phe Glu Gln Leu Lys Thr Asp Asp Ser Ala Gln
                165                 170                 175
Gly Leu Asp Asp Glu Gln Ser Ala Lys Arg Gln Ser Met Leu Asp Glu
                180                 185                 190
Ile Glu Arg Asp Phe Glu Ala Ala Thr Lys Gly Leu Glu Gln Leu Lys
                195                 200                 205
Ala Asp Asp Leu Thr Gly Ile Asn Asp Glu Glu His Ala Ala Lys Arg
210                 215                 220
Gln Lys Met Leu Glu Glu Ile Glu Arg Glu Phe Glu Glu Ala Thr Lys
225                 230                 235                 240
Gly Leu Glu Glu Leu Arg His Ser Thr Ser Ser Thr Asp Asp Glu Ala
                245                 250                 255
Gln Ser Ala Lys Arg Gln Asn Met Leu Asp Glu Ile Glu Arg Glu Phe
                260                 265                 270
Glu Ala Ala Thr Ser Gly Leu Lys Glu Leu Lys Ile Asn Ala His Thr
                275                 280                 285
Val Lys Asp Asp Val Asp Asp Lys Glu Gln Asp Ala Lys Arg Gln Ser
                290                 295                 300
Met Leu Asp Ala Ile Glu Arg Glu Phe Glu Ala Val Thr Glu Ser Phe
305                 310                 315                 320
Lys Gln Leu Glu Asp Ile Ala Asp Asn Lys Ala Glu Gly Asp Asp Glu
                325                 330                 335
Ser Ala Lys Arg Gln Ser Met Leu Asp Glu Ile Glu Arg Glu Phe Glu
                340                 345                 350
Ala Ala Thr Asn Ser Leu Lys Gln Leu Asn Leu Asp Asp Phe Ser Glu
                355                 360                 365
Gly Asp Asp Ser Ala Glu Ser Ala Arg Arg Asn Ser Met Leu Glu Ala
                370                 375                 380
Ile Glu Arg Glu Phe Glu Ala Ala Thr Lys Gly Leu Glu Glu Leu Lys
385                 390                 395                 400
Ala Asn Asp Ser Thr Gly Asp Lys Asp Asp Glu His Val Ala Arg
                405                 410                 415
Arg Lys Ile Met Leu Glu Ala Ile Glu Arg Glu Phe Glu Ala Ala Thr
                420                 425                 430
Lys Gly Leu Glu Glu Leu Lys Asn Glu Ser Glu Gln Ala Glu Asn Lys
                435                 440                 445
Arg Asn Ser Met Leu Glu Ala Phe Glu Arg Glu Phe Glu Ala Ala Thr
                450                 455                 460
```

```
Asn Ala Lys Ala Asn Gly Glu Asn Ser Ala Lys Asn Pro Ser Thr Ile
465                 470                 475                 480

Ser Thr Thr Val Gln Lys Ser Gly Gly Tyr Asn Ala Gly Leu Glu
                485                 490                 495

Gly Leu Leu Lys Pro Ala Asp Gly Val Cys Gly Cys Phe Asn Lys Asp
            500                 505                 510

Lys Asp Gly Leu Gln Ala Asp Thr Asp Ser Ser Ile Asn Ile Ala Glu
            515                 520                 525

Ile Leu Ala Glu Glu Ser Lys Leu Gln Gly Ser Gly Thr Ser Arg Leu
530                 535                 540

Thr Thr Ser Leu Asn Asn Leu Val Asp Thr His Arg Lys Glu Thr Ser
545                 550                 555                 560

Ser Lys Val Gly Ser Val Leu Gly Ser Ser Ser Val Thr Ser Thr
                565                 570                 575

Thr Ser Glu Ser Ala Ala Thr Ser Glu Ser Ile Glu Ser Leu Lys Gln
            580                 585                 590

Thr Leu Arg Lys Leu Arg Gly Leu Ser Ala Arg Asp Leu Val Asn His
        595                 600                 605

Pro Asn Phe Asp Ala Ile Ala Ala Gly Thr Arg Tyr Glu Val Leu
    610                 615                 620

Ser Ser Ala Ser Ile Gly Tyr Ile Ser Leu Leu Ala Lys Tyr Lys Thr
625                 630                 635                 640

Val Ile Lys Glu Gly Leu Glu Ala Ser Gln Arg Val Gln Ile Ala Gln
                645                 650                 655

Thr Arg Ala Lys Leu Leu Lys Glu Thr Ala Met Glu Lys Gln Arg Thr
            660                 665                 670

Val Asp Ser Val Phe Ala Ala Lys Thr Thr Ala Gln Arg Gly Asp
    675                 680                 685

Ala Leu His Ile Arg Ile Val Ala Ile Lys Lys Leu Leu Ala Lys Leu
        690                 695                 700

Glu Ala Glu Lys Val Asp Val Asp Ser Lys Phe Thr Ser Leu Thr Thr
705                 710                 715                 720

Ser Leu Ser Glu Leu Leu Lys Glu Ala Ser Gln Ala Tyr Glu Glu Tyr
                725                 730                 735

His Glu Ala Val His Lys Ala Lys Asp Glu Gln Ala Ala Glu Glu Phe
            740                 745                 750

Ala Val Glu Thr Thr Lys Arg Ala Glu His Ile Trp Val Glu Phe Leu
        755                 760                 765

Ser Ser Leu Asn
    770

<210> SEQ ID NO 7
<211> LENGTH: 1158
<212> TYPE: DNA
<213> ORGANISM: Arabidopsis thaliana
<220> FEATURE:
<221> NAME/KEY: misc_feature
<223> OTHER INFORMATION: AT3G28300
<220> FEATURE:
<221> NAME/KEY: CDS
<222> LOCATION: (1)..(1158)

<400> SEQUENCE: 7 atg gtg cta tcc aaa gag aat atg ttg aaa tac tcg gca cac ctt cgt    48
Met Val Leu Ser Lys Glu Asn Met Leu Lys Tyr Ser Ala His Leu Arg
1               5                  10                  15
```

```
gct tac aat tcc gca tgt gga gac cat cca gaa ctc aaa tcc ttt gat      96
Ala Tyr Asn Ser Ala Cys Gly Asp His Pro Glu Leu Lys Ser Phe Asp
             20                  25                  30 tct gag ctt cag cag aaa acc tca aat ctg ata aac tcg ttc acc tct     144
Ser Glu Leu Gln Gln Lys Thr Ser Asn Leu Ile Asn Ser Phe Thr Ser
         35                  40                  45 gat gcc aaa act ggg ttg gtg cca ctg ccc caa cac gca gca tac aag     192
Asp Ala Lys Thr Gly Leu Val Pro Leu Pro Gln His Ala Ala Tyr Lys
 50                  55                  60 gag ttc acc aag cac cta gct gaa gta aac caa cag gtg tca gac tac     240
Glu Phe Thr Lys His Leu Ala Glu Val Asn Gln Gln Val Ser Asp Tyr
 65                  70                  75                  80 atc att gga tat gga gaa gta gtg tgg gag aac tca act ctg aga tct     288
Ile Ile Gly Tyr Gly Glu Val Val Trp Glu Asn Ser Thr Leu Arg Ser
                 85                  90                  95 ttg gtc gaa acc tat ttt gaa agt gcc aag aag act ttg gac att gcc     336
Leu Val Glu Thr Tyr Phe Glu Ser Ala Lys Lys Thr Leu Asp Ile Ala
            100                 105                 110 gag aat gta aca gaa tac gtc gat gaa gca aaa agg ggc gaa cgt tac     384
Glu Asn Val Thr Glu Tyr Val Asp Glu Ala Lys Arg Gly Glu Arg Tyr
        115                 120                 125 att gta gcg gcc gtg gca cag ttt gaa aaa gac aaa gaa aat gat gtt     432
Ile Val Ala Ala Val Ala Gln Phe Glu Lys Asp Lys Glu Asn Asp Val
130                 135                 140 ggc aaa aaa acg aag agg tat gaa aat acc ttg agg gag ctg aag aag     480
Gly Lys Lys Thr Lys Arg Tyr Glu Asn Thr Leu Arg Glu Leu Lys Lys
145                 150                 155                 160 ttt gaa gcc atg gga aat cct ttt gat ggc gat aag ttc acg act ctg     528
Phe Glu Ala Met Gly Asn Pro Phe Asp Gly Asp Lys Phe Thr Thr Leu
                165                 170                 175 ttc aag ttg atg cac aag gag caa gaa tcc ctt ctg gaa aga gtg agg     576
Phe Lys Leu Met His Lys Glu Gln Glu Ser Leu Leu Glu Arg Val Arg
            180                 185                 190 gag act aag gaa aag ctt gat gag gaa ctt aaa aat att gag atg gaa     624
Glu Thr Lys Glu Lys Leu Asp Glu Glu Leu Lys Asn Ile Glu Met Glu
        195                 200                 205 ata agt agt cga aag aaa tgg agt ata att tcg aat gtg ctt ttc atc     672
Ile Ser Ser Arg Lys Lys Trp Ser Ile Ile Ser Asn Val Leu Phe Ile
210                 215                 220 ggt gcg ttt gtt gct gtt gcc gtc gga tcc atg gtt cta gta tgt aca     720
Gly Ala Phe Val Ala Val Ala Val Gly Ser Met Val Leu Val Cys Thr
225                 230                 235                 240 ggc gtg ggt gcg ggc gtg ggc gtt gca ggg ctt cta tca tta cca ctg     768
Gly Val Gly Ala Gly Val Gly Val Ala Gly Leu Leu Ser Leu Pro Leu
                245                 250                 255 att gcg ata gga tgg gta ggc gtc cac act att tta gag aac aag att     816
Ile Ala Ile Gly Trp Val Gly Val His Thr Ile Leu Glu Asn Lys Ile
            260                 265                 270 caa gct cga gag aaa cag gaa gaa gct ctg aag aaa gcg cac cgt ata     864
Gln Ala Arg Glu Lys Gln Glu Glu Ala Leu Lys Lys Ala His Arg Ile
        275                 280                 285 gca aac gaa atg gat aag ggt atg gaa acc gac aaa gta gat atg aat     912
Ala Asn Glu Met Asp Lys Gly Met Glu Thr Asp Lys Val Asp Met Asn
290                 295                 300 tcc ata tct gga aaa gtc cac gcg cta aaa agc aag atc acg tct atg     960
Ser Ile Ser Gly Lys Val His Ala Leu Lys Ser Lys Ile Thr Ser Met
305                 310                 315                 320 ttg aat gct gtg aag gat gct act gag gat gga gca aat gag gtg gac    1008
Leu Asn Ala Val Lys Asp Ala Thr Glu Asp Gly Ala Asn Glu Val Asp
                325                 330                 335
```

-continued

```
acg aaa caa gta atg gaa acc ctt acg ggg gac gtg gtg gaa tta aca    1056
Thr Lys Gln Val Met Glu Thr Leu Thr Gly Asp Val Val Glu Leu Thr
        340                 345                 350 gag gat atc aaa gca gtt ggt gat gat gtg gca aaa tat agc aaa atg    1104
Glu Asp Ile Lys Ala Val Gly Asp Asp Val Ala Lys Tyr Ser Lys Met
355                 360                 365 atc gaa gag acg agt tat cac gtt ttg caa aag atc act ggt tct gga    1152
Ile Glu Glu Thr Ser Tyr His Val Leu Gln Lys Ile Thr Gly Ser Gly
    370                 375                 380 aaa taa                                                             1158
Lys
385

<210> SEQ ID NO 8
<211> LENGTH: 385
<212> TYPE: PRT
<213> ORGANISM: Arabidopsis thaliana

<400> SEQUENCE: 8

Met Val Leu Ser Lys Glu Asn Met Leu Lys Tyr Ser Ala His Leu Arg
1               5                   10                  15

Ala Tyr Asn Ser Ala Cys Gly Asp His Pro Glu Leu Lys Ser Phe Asp
            20                  25                  30

Ser Glu Leu Gln Gln Lys Thr Ser Asn Leu Ile Asn Ser Phe Thr Ser
        35                  40                  45

Asp Ala Lys Thr Gly Leu Val Pro Leu Pro Gln His Ala Ala Tyr Lys
    50                  55                  60

Glu Phe Thr Lys His Leu Ala Glu Val Asn Gln Val Ser Asp Tyr
65                  70                  75                  80

Ile Ile Gly Tyr Gly Glu Val Val Trp Glu Asn Ser Thr Leu Arg Ser
                85                  90                  95

Leu Val Glu Thr Tyr Phe Glu Ser Ala Lys Lys Thr Leu Asp Ile Ala
            100                 105                 110

Glu Asn Val Thr Glu Tyr Val Asp Glu Ala Lys Arg Gly Glu Arg Tyr
        115                 120                 125

Ile Val Ala Ala Val Ala Gln Phe Glu Lys Asp Lys Glu Asn Asp Val
    130                 135                 140

Gly Lys Lys Thr Lys Arg Tyr Glu Asn Thr Leu Arg Glu Leu Lys Lys
145                 150                 155                 160

Phe Glu Ala Met Gly Asn Pro Phe Asp Gly Asp Lys Phe Thr Thr Leu
                165                 170                 175

Phe Lys Leu Met His Lys Glu Gln Glu Ser Leu Leu Glu Arg Val Arg
            180                 185                 190

Glu Thr Lys Glu Lys Leu Asp Glu Glu Leu Lys Asn Ile Glu Met Glu
        195                 200                 205

Ile Ser Ser Arg Lys Lys Trp Ser Ile Ile Ser Asn Val Leu Phe Ile
    210                 215                 220

Gly Ala Phe Val Ala Val Ala Val Gly Ser Met Val Leu Val Cys Thr
225                 230                 235                 240

Gly Val Gly Ala Gly Val Gly Val Ala Gly Leu Leu Ser Leu Pro Leu
                245                 250                 255

Ile Ala Ile Gly Trp Val Gly Val His Thr Ile Leu Glu Asn Lys Ile
            260                 265                 270

Gln Ala Arg Glu Lys Gln Glu Glu Ala Leu Lys Lys Ala His Arg Ile
        275                 280                 285
```

```
Ala Asn Glu Met Asp Lys Gly Met Glu Thr Asp Lys Val Asp Met Asn
    290                 295                 300
Ser Ile Ser Gly Lys Val His Ala Leu Lys Ser Lys Ile Thr Ser Met
305                 310                 315                 320
Leu Asn Ala Val Lys Asp Ala Thr Glu Asp Gly Ala Asn Glu Val Asp
                325                 330                 335
Thr Lys Gln Val Met Glu Thr Leu Thr Gly Asp Val Val Glu Leu Thr
            340                 345                 350
Glu Asp Ile Lys Ala Val Gly Asp Asp Val Ala Lys Tyr Ser Lys Met
        355                 360                 365
Ile Glu Glu Thr Ser Tyr His Val Leu Gln Lys Ile Thr Gly Ser Gly
370                 375                 380
Lys
385

<210> SEQ ID NO 9
<211> LENGTH: 1158
<212> TYPE: DNA
<213> ORGANISM: Arabidopsis thaliana
<220> FEATURE:
<221> NAME/KEY: misc_feature
<223> OTHER INFORMATION: AT3G28290
<220> FEATURE:
<221> NAME/KEY: CDS
<222> LOCATION: (1)..(1158)

<400> SEQUENCE: 9 atg gtg cta tcc aaa gag aat atg ttg aaa tac tcg gca cac ctt cgt      48
Met Val Leu Ser Lys Glu Asn Met Leu Lys Tyr Ser Ala His Leu Arg
1               5                   10                  15 gct tac aat tcc gca tgt gga gac cat cca gaa ctc aaa tcc ttt gat      96
Ala Tyr Asn Ser Ala Cys Gly Asp His Pro Glu Leu Lys Ser Phe Asp
            20                  25                  30 tct gag ctt cag cag aaa acc tca aat ctg ata aac tcg ttc acc tct     144
Ser Glu Leu Gln Gln Lys Thr Ser Asn Leu Ile Asn Ser Phe Thr Ser
        35                  40                  45 gat gcc aaa act ggg ttg gtg cca ctg ccc caa cac gca gca tac aag     192
Asp Ala Lys Thr Gly Leu Val Pro Leu Pro Gln His Ala Ala Tyr Lys
    50                  55                  60 gag ttc acc aag cac cta gct gaa gta aac caa cag gtg tca gac tac     240
Glu Phe Thr Lys His Leu Ala Glu Val Asn Gln Gln Val Ser Asp Tyr
65                  70                  75                  80 atc att gga tat gga gaa gta gtg tgg gag aac tca act ctg aga tct     288
Ile Ile Gly Tyr Gly Glu Val Val Trp Glu Asn Ser Thr Leu Arg Ser
                85                  90                  95 ttg gtc gaa acc tat ttt gaa agt gcc aag aag act ttg gac att gcc     336
Leu Val Glu Thr Tyr Phe Glu Ser Ala Lys Lys Thr Leu Asp Ile Ala
            100                 105                 110 gag aat gta aca gaa tac gtc gat gaa gca aaa agg ggc gaa cgt tac     384
Glu Asn Val Thr Glu Tyr Val Asp Glu Ala Lys Arg Gly Glu Arg Tyr
        115                 120                 125 att gta gcg gcc gtg gca cag ttt gaa aaa gac aaa gaa aat gat gtt     432
Ile Val Ala Ala Val Ala Gln Phe Glu Lys Asp Lys Glu Asn Asp Val
    130                 135                 140 ggc aaa aaa acg aag agg tat gaa aat acc ttg agg gag ctg aag aag     480
Gly Lys Lys Thr Lys Arg Tyr Glu Asn Thr Leu Arg Glu Leu Lys Lys
145                 150                 155                 160 ttt gaa gcc atg gga aat cct ttt gat ggc gat aag ttc acg act ctg     528
Phe Glu Ala Met Gly Asn Pro Phe Asp Gly Asp Lys Phe Thr Thr Leu
                165                 170                 175
```

-continued

| | |
|---|---|
| ttc aag ttg atg cac aag gag caa gaa tcc ctt ctg gaa aga gtg agg<br>Phe Lys Leu Met His Lys Glu Gln Glu Ser Leu Leu Glu Arg Val Arg<br>            180                        185                        190 | 576 |
| gag act aag gaa aag ctt gat gag gaa ctt aaa aat att gag atg gaa<br>Glu Thr Lys Glu Lys Leu Asp Glu Glu Leu Lys Asn Ile Glu Met Glu<br>195                        200                        205 | 624 |
| ata agt agt cga aag aaa tgg agt ata att tcg aat gtg ctt ttc atc<br>Ile Ser Ser Arg Lys Lys Trp Ser Ile Ile Ser Asn Val Leu Phe Ile<br>210                        215                        220 | 672 |
| ggt gcg ttt gtt gct gtt gcc gtc gga tcc atg gtt cta gta tgt aca<br>Gly Ala Phe Val Ala Val Ala Val Gly Ser Met Val Leu Val Cys Thr<br>225                        230                        235                        240 | 720 |
| ggc gtg ggt gcg ggc gtg ggc gtt gca ggg ctt cta tca tta cca ctg<br>Gly Val Gly Ala Gly Val Gly Val Ala Gly Leu Leu Ser Leu Pro Leu<br>                        245                        250                        255 | 768 |
| att gcg ata gga tgg gta ggc gtc cac act att tta gag aac aag att<br>Ile Ala Ile Gly Trp Val Gly Val His Thr Ile Leu Glu Asn Lys Ile<br>            260                        265                        270 | 816 |
| caa gct cga gag aaa cag gaa gaa gct ctg aag aaa gcg cac cgt ata<br>Gln Ala Arg Glu Lys Gln Glu Glu Ala Leu Lys Lys Ala His Arg Ile<br>275                        280                        285 | 864 |
| gca aac gaa atg gat aag ggt atg gaa acc gac aaa gta gat atg aat<br>Ala Asn Glu Met Asp Lys Gly Met Glu Thr Asp Lys Val Asp Met Asn<br>290                        295                        300 | 912 |
| tcc ata tct gga aaa gtc cac gcg cta aaa agc aag atc acg tct atg<br>Ser Ile Ser Gly Lys Val His Ala Leu Lys Ser Lys Ile Thr Ser Met<br>305                        310                        315                        320 | 960 |
| ttg aat gct gtg aag gat gct act gag gat gga gca aat gag gtg gac<br>Leu Asn Ala Val Lys Asp Ala Thr Glu Asp Gly Ala Asn Glu Val Asp<br>                        325                        330                        335 | 1008 |
| acg aaa caa gta atg gaa acc ctt acg ggg gac gtg gtg gaa tta aca<br>Thr Lys Gln Val Met Glu Thr Leu Thr Gly Asp Val Val Glu Leu Thr<br>                  340                        345                        350 | 1056 |
| gag gat atc aaa gca gtt ggt gat gat gtg gca aaa tat agc aaa atg<br>Glu Asp Ile Lys Ala Val Gly Asp Asp Val Ala Lys Tyr Ser Lys Met<br>355                        360                        365 | 1104 |
| atc gaa gag acg agt tat cac gtt ttg caa aag atc act ggt tct gga<br>Ile Glu Glu Thr Ser Tyr His Val Leu Gln Lys Ile Thr Gly Ser Gly<br>            370                        375                        380 | 1152 |
| aaa taa<br>Lys<br>385 | 1158 |

<210> SEQ ID NO 10
<211> LENGTH: 385
<212> TYPE: PRT
<213> ORGANISM: Arabidopsis thaliana

<400> SEQUENCE: 10

Met Val Leu Ser Lys Glu Asn Met Leu Lys Tyr Ser Ala His Leu Arg
1                 5                      10                    15

Ala Tyr Asn Ser Ala Cys Gly Asp His Pro Glu Leu Lys Ser Phe Asp
                    20                      25                    30

Ser Glu Leu Gln Gln Lys Thr Ser Asn Leu Ile Asn Ser Phe Thr Ser
            35                      40                      45

Asp Ala Lys Thr Gly Leu Val Pro Leu Pro Gln His Ala Ala Tyr Lys
     50                    55                      60

Glu Phe Thr Lys His Leu Ala Glu Val Asn Gln Gln Val Ser Asp Tyr
65                70                      75                    80

Ile Ile Gly Tyr Gly Glu Val Val Trp Glu Asn Ser Thr Leu Arg Ser
            85                  90                  95

Leu Val Glu Thr Tyr Phe Glu Ser Ala Lys Lys Thr Leu Asp Ile Ala
            100                 105                 110

Glu Asn Val Thr Glu Tyr Val Asp Glu Ala Lys Arg Gly Glu Arg Tyr
            115                 120                 125

Ile Val Ala Ala Val Ala Gln Phe Glu Lys Asp Lys Glu Asn Asp Val
            130                 135                 140

Gly Lys Lys Thr Lys Arg Tyr Glu Asn Thr Leu Arg Glu Leu Lys Lys
145                 150                 155                 160

Phe Glu Ala Met Gly Asn Pro Phe Asp Gly Asp Lys Phe Thr Thr Leu
                165                 170                 175

Phe Lys Leu Met His Lys Glu Gln Glu Ser Leu Leu Glu Arg Val Arg
            180                 185                 190

Glu Thr Lys Glu Lys Leu Asp Glu Glu Leu Lys Asn Ile Glu Met Glu
            195                 200                 205

Ile Ser Ser Arg Lys Lys Trp Ser Ile Ile Ser Asn Val Leu Phe Ile
            210                 215                 220

Gly Ala Phe Val Ala Val Ala Val Gly Ser Met Val Leu Val Cys Thr
225                 230                 235                 240

Gly Val Gly Ala Gly Val Gly Val Ala Gly Leu Leu Ser Leu Pro Leu
                245                 250                 255

Ile Ala Ile Gly Trp Val Gly Val His Thr Ile Leu Glu Asn Lys Ile
                260                 265                 270

Gln Ala Arg Glu Lys Gln Glu Glu Ala Leu Lys Ala His Arg Ile
            275                 280                 285

Ala Asn Glu Met Asp Lys Gly Met Glu Thr Asp Lys Val Asp Met Asn
290                 295                 300

Ser Ile Ser Gly Lys Val His Ala Leu Lys Ser Lys Ile Thr Ser Met
305                 310                 315                 320

Leu Asn Ala Val Lys Asp Ala Thr Glu Asp Gly Ala Asn Glu Val Asp
            325                 330                 335

Thr Lys Gln Val Met Glu Thr Leu Thr Gly Asp Val Val Glu Leu Thr
            340                 345                 350

Glu Asp Ile Lys Ala Val Gly Asp Asp Val Ala Lys Tyr Ser Lys Met
            355                 360                 365

Ile Glu Glu Thr Ser Tyr His Val Leu Gln Lys Ile Thr Gly Ser Gly
            370                 375                 380

Lys
385

<210> SEQ ID NO 11
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 11
aaaaagcagg cttcatggcg ttatccaaag at          32

<210> SEQ ID NO 12
<211> LENGTH: 31
<212> TYPE: DNA
<213> ORGANISM: Artificial sequence
<220> FEATURE:
<223> OTHER INFORMATION: Synthetic oligonucleotide -continued

```
<400> SEQUENCE: 12
agaaagctgg gtcttaacgg ttgatctttt g                                      31

<210> SEQ ID NO 13
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 13
agaaagctgg gtcacggttg atcttttg                                          28

<210> SEQ ID NO 14
<211> LENGTH: 33
<212> TYPE: DNA
<213> ORGANISM: Artificial sequence
<220> FEATURE:
<223> OTHER INFORMATION: Synthetic oligonucleotide

<400> SEQUENCE: 14
agaaagctgg gtctattttt tctctagatt act                                    33

<210> SEQ ID NO 15
<211> LENGTH: 32
<212> TYPE: DNA
<213> ORGANISM: Artificial sequence
<220> FEATURE:
<223> OTHER INFORMATION: Synthetic oligonucleotide

<400> SEQUENCE: 15
aaaaagcagg cttcccatga agataatgag gc                                     32

<210> SEQ ID NO 16
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 16
agaaagctgg gttcacgaat atacgggata g                                      31

<210> SEQ ID NO 17
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 17
caccatggga acaaagtttt ta                                                22

<210> SEQ ID NO 18
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 18
tcaattaagt gaactaagaa actcaac                                           27

<210> SEQ ID NO 19
```

<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 19
aaaaagcagg cttcatggcg atgaggggct tc                          32

<210> SEQ ID NO 20
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 20
agaaagctgg gttcagagct catccttgac                             30

<210> SEQ ID NO 21
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 21
tctccaacca ccatggcgtt a                                      21

<210> SEQ ID NO 22
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 22
gaaagctggg taacggttga tctt                                   24

<210> SEQ ID NO 23
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 23
tctccaacca ccatggaaat c                                      21

<210> SEQ ID NO 24
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 24
gaaagctggg taaagagaac taag                                   24

<210> SEQ ID NO 25
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 25

```
tccaaccacc atgggaac                                              18

<210> SEQ ID NO 26
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 26
gaaagctggg taattaagtg aactaag                                    27

<210> SEQ ID NO 27
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 27
tctccaacca ccatggcgat g                                          21

<210> SEQ ID NO 28
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 28
gaaagctggg tagagctcat ccttgac                                    27

<210> SEQ ID NO 29
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 29
tctccaacca ccatgaccgg                                            20

<210> SEQ ID NO 30
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 30
gaaagctggg taaagtaagc cagcaag                                    27

<210> SEQ ID NO 31
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 31
acaagtttgt acaaaaaagc aggctctcca accacc                          36

<210> SEQ ID NO 32
<211> LENGTH: 39
<212> TYPE: DNA
```

```
<213> ORGANISM: Artificial Sequence
<220> FEATURE:
<223> OTHER INFORMATION: Synthetic oligonucleotide

<400> SEQUENCE: 32
tccgccacca ccaaccactt tgtacaagaa agctgggta                            39

<210> SEQ ID NO 33
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 33
ggggacaagt ttgtacaaaa aagcaggct                                      29

<210> SEQ ID NO 34
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 34
ggggaccact ttgtacaaga aagctgggt                                      29

<210> SEQ ID NO 35
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 35
tcgcgttaac gctagcatgg atctc                                          25

<210> SEQ ID NO 36
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 36
gtaacatcag agattttgag acac                                           24

<210> SEQ ID NO 37
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 37
gcgaatacgg tggtgaaagt                                                20

<210> SEQ ID NO 38
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 38
gcagcttgtg ttatggagca                                                20
```

<210> SEQ ID NO 39
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 39
gagaatatgg cggtgacgat                                              20

<210> SEQ ID NO 40
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 40
gatgtggtcg tccatgtgag                                              20

<210> SEQ ID NO 41
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 41
tgttgactct gcctcaatcg                                              20

<210> SEQ ID NO 42
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 42
cagccaggtc ctccagttag                                              20

<210> SEQ ID NO 43
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 43
ggtggttcat caaacccaag                                              20

<210> SEQ ID NO 44
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 44
cttttggagt tgctgccttc                                              20

<210> SEQ ID NO 45
<211> LENGTH: 20
<212> TYPE: DNA
<213> ORGANISM: Artificial Sequence
<220> FEATURE:

<223> OTHER INFORMATION: Synthetic oligonucleotide

<400> SEQUENCE: 45
gaccgaaaac tccagaccaa                                              20

<210> SEQ ID NO 46
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 46
ttcaggaacg tgttggatca                                              20

<210> SEQ ID NO 47
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 47
tttgggtgat gtctttcatc at                                           22

<210> SEQ ID NO 48
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 48
cttggaggaa gcttgtcagc                                              20

<210> SEQ ID NO 49
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 49
gaaaaattgc tccccacaaa                                              20

<210> SEQ ID NO 50
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 50
gctttggtac gacacagcaa                                              20

<210> SEQ ID NO 51
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 51
tgcaaagaat ccatcaacca                                              20

```
<210> SEQ ID NO 52
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 52
cctgagccct gtaatttgga                                               20

<210> SEQ ID NO 53
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 53
gcctcaaaaa gacggacaag                                               20

<210> SEQ ID NO 54
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 54
gacgcagcag agcaagtaga                                               20

<210> SEQ ID NO 55
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 55
ccgtggacat gtcaatcatc                                               20

<210> SEQ ID NO 56
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 56
tgttcatcga cgaaacgaag                                               20

<210> SEQ ID NO 57
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 57
attggaaacg gatatgctcc a                                             21

<210> SEQ ID NO 58
<211> LENGTH: 21
<212> TYPE: DNA
```

```
<213> ORGANISM: Artificial Sequence
<220> FEATURE:
<223> OTHER INFORMATION: Synthetic oligonucleotide

<400> SEQUENCE: 58
tccttacctg aacgcctgtc a                                              21
```

DROUGHT-TOLERANT TRANSGENIC PLANT

CROSS REFERENCE TO RELATED APPLICATION

This application claims priority to U.S. Provisional Application No. 62/056,099, filed on Sep. 26, 2014, the content of which is hereby incorporated by reference herein in its entirety.

BACKGROUND

Even relatively mild water limitation that causes reduced soil water potential ($\psi_w$) during drought can dramatically reduce plant growth and agricultural productivity. Detailed physiological analyses have shown that plant growth is actively down regulated during drought and not limited by carbon supply. The sensitivity of growth to low water potential has a wide range of genetic variabilities depending on the drought adaptation strategy employed by a specific plant genotype. Also, there are many specific metabolic pathways, for example proline metabolism, that are highly regulated by stress and contribute to stress tolerance. A strong reduction in growth in response to mild or moderate stress can help ensure survival by conserving water. However, it can be undesirable for agriculture as plant productivity is reduced more than it need be if growth were less sensitive to changes in water status.

SUMMARY

In one aspect, described below is a transgenic plant, comprising: (i) a recombinant DNA construct that contains a nucleic acid sequence operably linked to a promoter, the nucleic acid sequence encoding an AFL1 polypeptide, (ii) a recombinant DNA construct for inhibiting expression of a PD15 polypeptide or a NAI2 polypeptide, or (iii) a loss-of-function mutation in a PD15 gene or a NAI2 gene, wherein the transgenic plant exhibits increased growth under drought as compared to a control plant. The increased growth can include one of more of (i) increased fresh and/or dried plant weight; (ii) increased plant height; (iii) increased leaf area; (iv) increase seed yield, size and/or weight; (v) increased fruit yield, size and/or weight; (vi) increased panicle density and/or length; (vii) increased root elongation; (viii) increased or altered root branching; (ix) increased total root length; and (x) increased fresh and/or dried weight of plant root system. The transgenic plant can further exhibit increased proline accumulation under drought as compared to the control plant.

In one embodiment, the AFL1 polypeptide has an amino acid sequence that is at least 80% (e.g., 85%, 90%, 95%, or 99%) identical to the sequence of SEQ ID NO:2. The AFL1 polypeptide can also be a homolog of the AFL1 polypeptide. In another embodiment, the PD15 polypeptide has an amino acid sequence that is at least 80% (e.g., 85%, 90%, 95%, or 99%) identical to that of SEQ ID NO:4. The NAI2 polypeptide can have an amino acid sequence that is at least 80% (e.g., 85%, 90%, 95%, or 99%) identical to that of SEQ ID NO:6.

The transgenic plant can be a crop such as tomato, canola, soybean, cotton, or alfalfa.

In another aspect, described herein is a method of producing a transgenic plant. The method includes introducing into a host plant (i) a recombinant DNA construct that contains a nucleic acid sequence operably linked to a promoter, the nucleic acid sequence encoding an AFL1 polypeptide, (ii) a recombinant DNA construct for inhibiting expression of a PD15 polypeptide or a NAI2 polypeptide, or (iii) a loss-of-function mutation in a PD15 gene or a NAI2 gene, and identifying a host plant that exhibits increased growth under drought, whereby the transgenic plant is produced.

In yet another aspect, a method of promoting plant growth in an area that is under drought, susceptible to drought, or under limited irrigation is described. The method includes cultivating the transgenic plant described herein in the area.

The details of one or more embodiments are set forth in the accompanying drawings and the description below. Other features, objects, and advantages of the embodiments will be apparent from the description and drawings, and from the claims.

DETAILED DESCRIPTION

Figure 1:
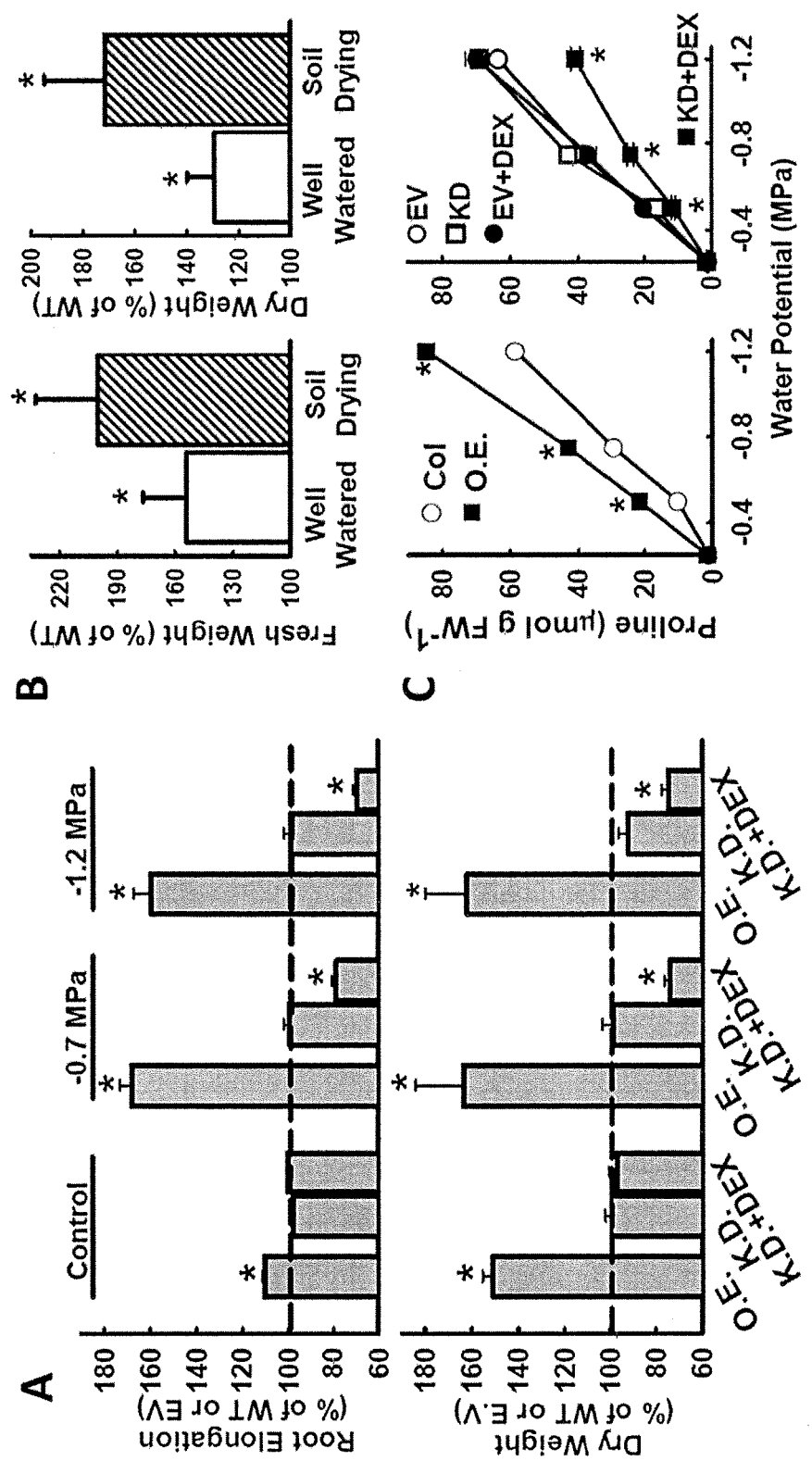
FIG. 1 is a set of graphs showing that AFL1 expression promotes plant growth during low water potential stress. (A): Root elongation and dry weight of AFL1 overexpression and RNAi knockdown plants after transfer to unstressed control media (0.25 MPa), an intermediate stress (−0.7 MPa) or more severe stress (−1.2 MPa). (B): Rosette fresh weight and dry weight of AFL1-overexpressing plants relative to those of wild type in well-watered and controlled drying soil. (C): Proline accumulation in AFL1-overexpressing and knock down lines across a range of low water potential severities. Col—wild type; O.E.—35S-mediated ectopic expression of AFL1; K.D.—DEX-inducible RNAi knockdown of AFL1; EV—empty vector control for K.D.

It was unexpectedly discovered that certain proteins are involved in plant drought tolerance. Therefore, described herein are transgenic plants that exhibit enhanced tolerance to drought.

Data described below show that overexpression of a membrane associated protein, At14a-like1 (AFL1), increased growth and accumulation of the osmoprotective solute proline and also altered the transcriptome response to low water potential stress in plants. At14a (At3g28300) was first identified by immunoscreening and Arabidopsis expression library with antisera recognizing mammalian $\beta_1$-Integrin and reported to be a plasma membrane associated protein. A cluster of At14a related genes, including AFL1, are present in Arabidopsis. Like At14a, AFL1 contains a small domain with similarity to integrins (Domain of Unknown Function 677) as well as two hydrophobic helices which presumably mediate its membrane localization.

Even though subcellular localization suggested a primarily plasma membrane localization of AFL1, it interacted with the endomembrane proteins Protein Disulfide Isomerase5 (PDI5) and the ER-body protein NAI2. These interactions were more prevalent during stress. PDI5 and NAI2 single and double mutants also exhibited increased growth and proline accumulation consistent with roles in the same stress signaling mechanisms as AFL1. AFL1 also interacted with Adaptor protein2-2A (AP2-2A) which is part of a protein complex that recruits proteins for endocytosis. AFL1 could be readily observed in punctae along the plasma membrane consistent with endocytotic vesicles and tyrphostin A21, an endocytosis inhibitor, blocked the increased proline accumulation induced by AFL1 overexpression. Co-localization of AFL1 with Clathrin light chain further indicated a function of AFL1 in endocytosis. AFL1 may be involved in the upstream events in drought sensing and is an attractive target for biotechnology as its overexpression can dramatically improve growth under drought without causing growth inhibition of unstressed plants.

A transgenic plant that expresses (e.g., overexpresses or constitutively expresses) an AFL1 polypeptide can be generated by introducing into a host plant or a part thereof an expression construct containing a DNA sequence encoding the AFL1 polypeptide. The DNA sequence is operably linked to regulatory sequences which are capable of directing the expression of the AFL1 polypeptide in the plant. These regulatory sequences can also include sequences capable of directing transcription in plants, either constitutively, or stage and/or tissue specific, depending on the use of the plant or parts thereof. The expression constructs can be introduced into the plant using methods known in the art or described below (e.g. via a T-DNA delivered by an Agrobacterium).

A transgenic plant that expresses a lower level of a PDI5 or a NAI2 polypeptide (or both) can also be constructed using methods known in the art. For example, a recombinant DNA construct that expresses an RNA molecule containing a nucleotide sequence complementary to the nucleotide sequence of a gene that encodes one of PDI5 or NAI2 can be introduced into a host plant. Such an RNA molecule can be an antisense RNA or an interfering RNA (e.g., a small interfering RNA). As used herein, the term "interfering RNA" means an RNA molecule capable of directing the degradation of an RNA transcript having a nucleotide sequence at least a portion of which is substantially the same as that of the interfering RNA, through the mechanism of RNA interference. An interfering RNA can be a small interfering RNA (siRNA), which includes two complementary single-stranded RNAs that form an intermolecular duplex. An interfering RNA can also be a short hairpin RNA (shRNA), which includes a single-stranded RNA with two self-complementary regions that allow the RNA to fold back upon itself and form a stem-loop structure with an intramolecular duplex region and an unpaired loop region. In some circumstances, interfering RNAs can be single-stranded antisense RNAs of 19 to 29 nucleotides that are complementary to a target sequence. See Martinez et al., Cell 110:563-574 (2002). In other instances, interfering RNAs are double-stranded RNAs that, upon cleavage in cells, produce siRNAs.

A transgenic plant with a loss-of-function mutation in its genomic PDI5 or NAI2 gene sequence can also be generated. For example, such a transgenic plant can have a deletion, insertion, or point mutation in its PDI5 or NAI2 gene. Genome editing technologies are known in the art, e.g., those that involve the clustered regularly interspersed short palindromic repeats/CRISPR-associated (CRISPR/Cas) system or transcription activator-like effector nucleases (TALENs). See, e.g., Feng et al., Cell Res., 23(10): 1229-1232 (2013).

As used herein, each of the terms "AFL1", "PDI5", and "NAI2" can refer to an *Arabidopsis* polypeptide or a variant or homolog thereof. *Arabidopsis* AFL1, PDI5, and NAI2 nucleic acid sequences (SEQ ID NOs:1, 3, and 5, respectively) and amino acid sequences (SEQ ID NOs:2, 4, 6, respectively) are provided herewith. Homologs of *Arabidopsis* AFL1 that can be overexpressed in a plant to enhance its drought tolerance include At3g28300 (SEQ ID Nos:7 and 8) and At3g28290 (SEQ ID Nos:9 and 10).

Under drought conditions, the transgenic plant described herein (e.g., one that overexpress an AFL1 protein or expresses a lower level of a PDI5 or NAI2 protein), as compared to a wild-type or untransformed host plant, exhibits one of more of the following characteristics: (1) increased fresh and/or dried plant weight; (2) increased plant height; (3) increased leaf area; (4) increase seed yield, size and/or weight; (5) increased fruit yield, size and/or weight; (6) increased panicle density and/or length; (7) increased root elongation; (8) increased or altered root branching; (9) increased total root length; and (10) increased fresh and/or dried weight of plant root system.

Such a transgenic plant can be used to promote plant growth and yield in suboptimal environments, particularly water limited environments (e.g., those under drought or susceptible to drought). As overexpression of AFL1 was shown not to limit, and may promote, growth in relatively unstressed environments as well as during water limitation, its use is particularly applicable to environments with sporadic drought where water limitation occurs during only part of the growing season or may be highly variable between growing seasons. Transgenic plants that express AFL1 can also be used in the development of "deficit irrigation" systems where plants are given only a limited amount of water to hold them at a moderate level of water limitation and prevent severe drought stress. In this situation, increased AFL1 expression would prevent down regulation of growth of partially irrigated plants. The combination of limited irrigation with water efficient plants can greatly increase the efficiency of water use per unit yield.

As used herein, the term "drought" can refer to artificially-created or natural drought. Drought conditions can include, for example, depletion of soil water content over the course of several days to a level 30-40% reduced from the water content of fully watered soil, transfer of a plant to agar solidified nutrient media with polyethylene glycol added to reduce water potential to the range of −0.5 to −1.2 MPa, and those conditions described in the examples below.

Whether an area or region is under drought can be determined by a person skilled in the art using art-recognized methodologies. Whether an area or a region is susceptible to drought can also be determined by a person skilled in the art and/or based on art-accepted criteria.

The transgenic plant described herein can be a crop. Crops include, but are not limited to, tomato, soy, cotton, canola, maize, wheat, sunflower, sorghum, alfalfa, barley, millet, rice, tobacco, fruit and vegetable crops, and turf grass.

The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications cited herein are herein incorporated by reference in their entirety.

EXAMPLES

Example 1: Materials and Methods

Transgenic Plants and T-DNA Mutants

Total RNA RNeasy Plant Mini Kit (Qiagen) was used according to the manufacturer's instructions. AFL1 was amplified using Phusion DNA polymerase (New England BioLabs) and gene specific primers containing part of the Gateway cloning sequences. See primer sequences in Table 1. A second nested PCR was performed to add the remaining Gateway cloning sequence and the PCR product was integrated into pDONOR 207 by BP reaction (Invitrogen). After sequencing, the AFL1 clone was transferred by LR reaction to pGWB412 or pGWB411 to generate N-terminal and C-terminal fusions of AFL1 to the FLAG epitope with expression driven by the 35S promoter. Likewise, 35S:YFP-AFL1 constructs were generated using the pGWB442 vector. pGWB vectors are previously described. These constructs were transferred to *Agrobacterium tumefacians* GV3101 and transformed into *Arabidopsis thaliana* Col-0 (hereafter referred to as wild type or W.T.) by floral dip transformation. Transgenic plants were selected by Kanamycin (50 μg ml$^{-1}$). Gene and protein expressions in transgenic lines were assayed using quantitative RT-PCR (QPCR) and immunoblotting using either a commercial antisera recognizing mammalian β-integrin or AFL1 specific antisera (see below). Homozygous $T_3$ lines were used for all further analyses.

TABLE 1

Primer sequences for cloning

| SEQ ID NO: | Atg# | Gene Name | Purpose | Forward/Reverse |
|---|---|---|---|---|
| 11 | AT3G28270 | AFL1 | Cloning full length AFL1 | forward |
| 12 | AT3G28270 | AFL1 | Cloning full length AFL1 | reverse |
| 11 | AT3G28270 (ΔSTOP) | AFL1 | Cloning full length AFL1- no stop codon | forward |
| 13 | AT3G28270 (ΔSTOP) | AFL1 | Cloning full length AFL1- no stop codon | reverse |
| 14 | AT3G28270 | AFL1 | Cloning AFL1 N-terminal fragment for protein expression and yeast two hybrid screen | reverse |
| 15 | AT3G28270 | AFL1 | Cloning AFL1 gene specific tag for RNAi | forward |
| 16 | AT3G28270 | AFL1 | Cloning AFL1 gene specific tag for RNAi | reverse |
| 17 | AT3G15950 | NAI2 | Full length clone | forward |
| 18 | AT3G15950 | NAI2 | Full length clone | reverse |
| 19 | AT1G21750 | PDI5 | Full length clone | forward |
| 20 | AT1G21750 | PDI5 | Full length clone | reverse |
| 21 | AT3G28270 | AFL1 | mbSUS yeast two hybrid clone | forward |
| 22 | AT3G28270 | AFL1 | mbSUS yeast two hybrid clone | reverse |
| 23 | AT1G52410 | TSA1 | mbSUS yeast two hybrid clone | Forward |
| 24 | AT1G52410 | TSA1 | mbSUS yeast two hybrid clone | Reverse |

TABLE 1-continued

Primer sequences for cloning

| SEQ ID NO: | Atg# | Gene Name | Purpose | Forward/Reverse |
|---|---|---|---|---|
| 25 | AT3G15950 | NAI2 | mbSUS yeast two hybrid clone | Forward |
| 26 | AT3G15950 | NAI2 | mbSUS yeast two hybrid clone | Reverse |
| 27 | AT1G21750 | PDI5 | mbSUS yeast two hybrid clone | Forward |
| 28 | AT1G21750 | PDI5 | mbSUS yeast two hybrid clone | Reverse |
| 29 | AT5G22780 | AP2 | mbSUS yeast two hybrid clone | Forward |
| 30 | AT5G22780 | AP2 | mbSUS yeast two hybrid clone | Reverse |
| 31 | | B1-linker | mbSUS cloning adapter | Forward |
| 32 | | B2-linker | mbSUS cloning adapter | Reverse |
| 33 | | attB1 | adapter primer for gateway cloning | forward |
| 34 | | attB2 | adapter primer for gateway cloning | reverse |
| 35 | | PDONR207 | vector primer for sequencing | forward |
| 36 | | PDONR207 | vector primer for sequencing | reverse |

To generate AFL1 knock down (K.D.) lines, a 301 bp Gene specific Tag (GST) sequence targeting the C-terminal region of AFL1 was selected using the CATMA database (found at the catma.org website) and an entry clone was made with pDONR 207 as described above. The C-terminal region of AFL1 was targeted for RNAi to maximize the specificity of the RNAi knockdown. This entry clone was initially transferred to the pAgrikola vector (see the agrikola.org website) for constitutive RNAi suppression of AFL1. However, we failed to recover transgenic lines with substantial suppression of AFL1 expression using this method. The same entry clone was then transferred to the pOpOff vector for Dexamethasone (DEX)-inducible RNA suppression of AFL1. Simultaneously, an empty vector was also made without the AFL1 sequence as negative control. After sequencing, the vectors were transferred to *Agrobacterium* and used to generate transgenic plants as described above. The effectiveness of the RNAi was confirmed by application of 10 µM DEX, transfer of seedlings to low water potential stress (see below) followed by QPCR and immunoblot analysis.

T-DNA mutants of PDI5 and NAI2 were obtained from the *Arabidopsis* Biological Resource Center (see Table 2) and homozygous lines confirmed by PCR genotype using primers from the Signal data base (see the signal.salk.edu website). RT-PCR was used to confirm absence of gene expression. All the physiological data described below are the combined data of two T-DNA alleles for pdi5 and nai2.

TABLE 2

T-DNA mutants

| Atg# | Gene name | Mutant ID | Insertion site (based on TAiR) |
|---|---|---|---|
| AT3G15950 | NAI2 | Salk_079469 | 5' UTR |
| AT3G15950 | NAI2 | Salk_043149 | last exon |
| AT1G21750 | PDI5 | Salk_015253 | third exon |
| AT1G21750 | PDI5 | Salk_136642 | second exon |

Figure 2:
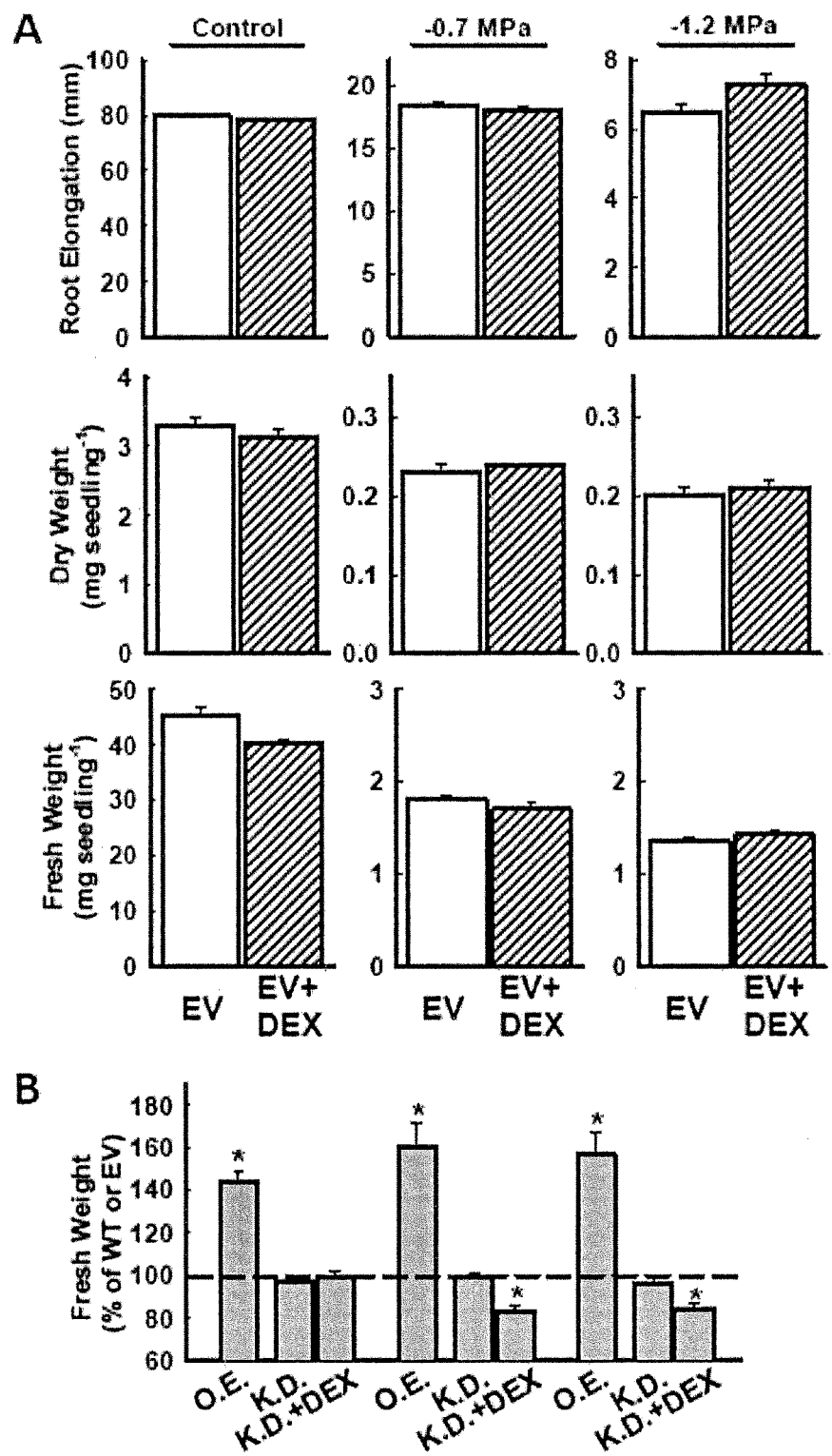
FIG. 2 is a set of graphs showing seedling growth of transgenic lines with increased or decreased AFL1 expression. (A): Root elongation, dry weight and fresh weight of EV. Application of DEX to EV had no effect on any of the growth parameters. All growth parameters for EV were essentially identical to those of the Col wild type used to normalize the growth data shown in FIG. 1, panel A. (B): Seedling fresh weight data from the same experiments as the root elongation and dry weight data shown in FIG. 1, panel A.
Figure 3:
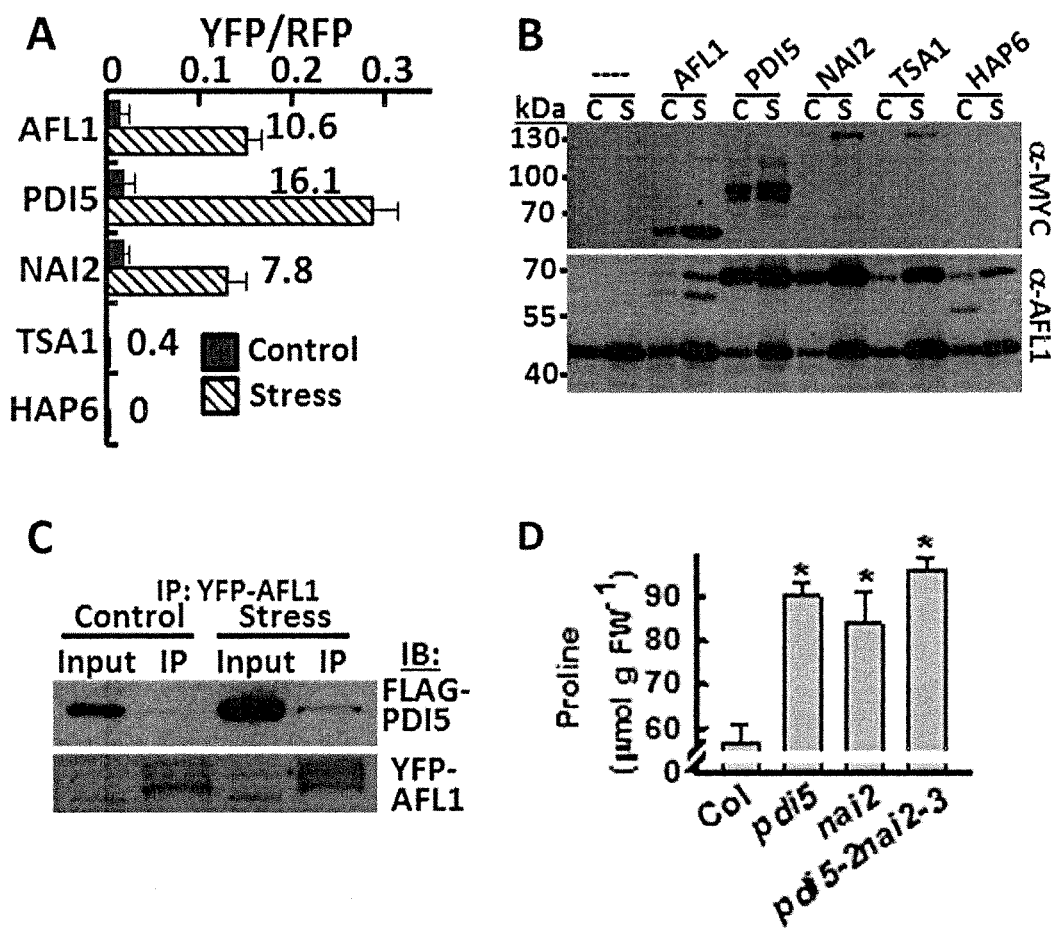
FIG. 3 includes blots and graphs showing that AFL1 has stress-enhanced interaction with ER signaling proteins PDI5 and NAI2, which act as negative regulators of growth and proline. (A): Relative BiFC signal for AFL1 interactions. The number by each bar indicates the fold increase of YFP/RFP ratio in stress versus control for each interaction. Data are ±S.E. (n=6 to 11). (B): Immunoblot of samples collected after rBiFC assay. Anti-MYC was used to detect the YFPC-protein fusions while AFL1 specific antisera were used to detect the YFPN-AFL1 fusion proteins. In the AFL1 blot both native AFL1 (47 kDa) and the AFL1 fusion protein (70 kDa) can be seen. For AFL1 interaction with itself, both the YFPN and YFPC fusion proteins were detected. C=unstressed control. S=low $\psi_w$ (water potential) stress treated. (C): Co-IP of PDI5-FLAG with YFP-AFL1 in control and stress treated seedlings. Three independent Co-IP experiments gave consistent results. (D): Proline accumulation of WT, pdi5 (combined data of pdi5-1 and pdi5-2), nai2 (combined data of nai2-1 and nai2-3) and pdi5-2nai2-3 at 96 h after transfer to −1.2 MPa. Data are means±S.E. (n=6-12 from 2 independent experiments). Significant differences compared to wild type are indicated by * (P≤0.05).

Plant Growth Conditions, Stress and Inhibitor Treatments, Growth and Proline Assays Plants were routinely propagated in a growth room at 23° C. and 16 h light period. For seedling experiments, seed was sterilized, plated on agar plates, stratified for 4 d and the plates incubated vertically in a growth chamber at 23° C. and continuous light (70-90 µmol photons $m^{-2}$ $sec^{-1}$) as previously described. See Kesari et al., PNAS 109: 9197-9202 (2012). The growth media consisted of half-strength MS media with 2 mM MES buffer (pH 5.7). No sugar was added to any of the plant growth media. Low water potential stress was imposed by transferring either 7-day-old (for proline and gene expression assays) or 4-day-old (for root elongation, fresh weight and dry weight measurements) to agar plates infused with PEG-8000 as previously described. See Verslues et al., The Plant Journal 45: 523-539 (2006). For root growth and fresh weight measurements, position of the apices was marked and root elongation measured over the subsequent 8 days after transfer. Fresh weight and dry weight were quantified at the end of each experiment. Root elongation (FIG. 1, panel A) was normalized to Col wild type and represents the combined data (means±S.E., n=12 from 2 independent experiments) of four independent overexpression or dexamethasone-inducible RNAi lines. Fresh weight and dry weight data (FIG. 1 and FIG. 2) were from the same experiments. Data were combined from four independent transgenic lines expressing either YFP-AFL1 or FLAG-AFL1. Proline was assayed by ninhydrin assay adapted to 96-well plate format. See Bates et al., Plant and Soil 39: 205-207 (1973); and R Sunkar, ed, Plant stress Tolerance. Methods and Protocols, Vol Methods in Molecular Biology Vol 639, Humana Press, New York, pp 301-316 (2010). Proline data in FIG. 1 are means±S.E., n=12-36, combined from two independent experiments. Data were combined from four lines expressing YFP-AFL1 or FLAG-AFL1 or four independent RNAi transgenic lines. Proline data of pdi5 and nai2 (FIG. 3) are combined data of two T-DNA mutant lines having the same phenotype (means±S.E., n=12-24).

For experiments with AFL1 K.D. lines, DEX pretreatment was performed by transferring 5 or 6 day-old plants to control plates with 10 µM DEX added. Seven day old seedlings were then transferred to either fresh DEX-containing control media or PEG-infused plates with DEX and samples were collected 96 h after transfer. For experiments measuring root elongation and plant weight, 4 day-old plants were transferred directly to 10 µM DEX media and were sprayed with 10 µM DEX on alternate days to maintain repression of AFL1. For inhibitor experiments, stocks of Tyrphostin A23 and its negative analog Tyrphostin A51 (Sigma) were made in DMSO, stored at −20° C. and added to either control or PEG-infused agar plates to a final concentration of 15 µM.

For soil drying experiments, potting mix was supplemented to 25% Turface (Turface Athletics, USA) to increase porosity, autoclaved, and distributed to 8 cm×8 cm×10 cm (L×W×H) plastic pots (180 g per pot). The soil-Turface mix was watered to saturation and four genotypes (wild type and three transgenic lines) planted in different sectors of the each pot. The pots were incubated in a short day growth chamber (8 h photoperiod; 100 µmol $m^{-2}$ $sec^{-1}$ light; 23° C.) and the plants thinned to one plant per sector. The pots were watered with Hyponex nutrient solution (manufacturer) diluted to 0.3 g $l^{-1}$. On the fifteenth day of growth, the pots were watered to saturation and allowed to drain completely over several hours. The weight of each pot was recorded. The pots were allowed to dry over the subsequent eight days. After eight days of drying, the pots were reweighed and watered (by injecting into the middle of the pot with a syringe) to bring each pot back to 75% of its initial weight. The pots were then allowed to dry for another 10 days. Control pots were maintained at fully saturated water content during this period. At the end of the drying period, rosette fresh weight (F.W.), hydrated. weight (H.W.; measured after floating rosettes on cold water for ~6 h) and dry weight (D.W.) were measured and relative water content calculated as (F.W.−D.W.)/(H.W.−D.W.)×100. Soil water potential was checked using a Psypro system with c52 sample chambers (Wescor) after collecting and well-mixing of soil samples from several pots. Water potentials at the end of the drying period range were approximately −1.4 MPa with most of the decrease in water potential occurring over the last few days of soil drying. Rosette F.W. and D.W. were normalized using the W.T. plants growing in the same pot. Rosette F.W. and D.W data shown in FIG. 1 represent means±S.E., n=10-12, combined from three independent experiments. Data were combined from three overexpression lines (expressing either YFP-AFL1 or FLAG-AFL1).

Recombinant Protein Production and Generation of AFL1 Antisera

AFL1-N terminal fragment (amino acids 1-208) was cloned into pDONR207 and transferred to pET300 (Invitrogen). His-tagged fusion proteins were produced in *Escherichia coli*, Rosetta strain (Novagen). Recombinant protein production was inducted by addition of 1 mM IPTG to late log phase cultures and incubation for 3 h at 37° C. Cells were harvested by centrifugation and disrupted using Constant Cell disruptor (Constant Systems TS Cell Disruptor, UK.). Recombinant protein was present in the insoluble fraction of the extract and was resolubilized using 8 M urea before being applied to HisPur Cobalt Spin columns (Thermo Scientific, USA) and purified protein eluted following the manufacturer's instructions. Protein purity was checked by SDS-PAGE and Coomassie staining before being used to generate polyclonal antisera. AFL1 polyclonal antisera was generated in rabbit by LTK Biolaboratories (Taiwan). Antibody titer was checked by immunoblotting blotting using the purified recombinant N-terminal AFL1 fragment as well as total protein extracts from control and stress treated seedlings.

Immunoblot Detection of AFL1

Samples (50-100 mg of seedlings) were grinded in liquid $N_2$ and 100 μL extraction buffer (125 mM Tris-Cl pH 8.8, 1% SDS, 10% glycerol and 1 mM PMSF, Complete Protease Inhibitor [Roche]) was added. Samples were centrifuged at 7000 g for 10 min and supernatant collected. Protein concentration was checked using Pierce BCA protein assay kit (Thermo Scientific, USA) and typically 50 μg protein was loaded onto 10% SDS-PAGE gels. Proteins were blotted onto PVDF membranes and probed with AFL1 antisera (1/5000) or an antisera recognizing mammalian $β_1$ integrin (GTX112971, GeneTex) at 1/3000 dilution. Tagged AFL1 from transgenic lines was detected with anti-FLAG (Sigma) or GFP antibodies (AB290 ABCAM). HRP-conjugated anti-rabbit secondary antibody was used and blots were developed with chemiluminescent substrate (Thermo Scientific) and exposed to film.

Yeast Two Hybrid Screening

A yeast two hybrid library was prepared using mRNA from seedlings exposed to −1.2 MPa low water potential stress for 96 h. The library was prepared using the Cloneminer II cDNA construction (Invitrogen) according to the manufacturer's instructions. Yeast two hybrid screening was performed using the ProQuest Two-hybrid system (Invitrogen) following manufacturer's instructions with an N-terminal fragment of AFL1 (amino acids 1 to 208) as bait. The bait fragment was cloned into destination vector pDEST23 and co-transformed into MaV203 along with clones from the cDNA library using LiAc X transformation. Transformed yeast cells were plated on SC-Leu-Trp-His with 55 mM 3-AT, as preliminary test found that this 3-AT concentration was sufficient to suppress autoactivation by the bait construct. Colonies that grew on the selective media were re-streaked and subjected to β-galactosidase filter assay to confirm interaction. Out of approximately $8 \times 10^5$ colony forming units screened, clones of PDI5, NAI2, and TSA1 were detected repeatedly. Most of these clones were C-terminal truncations. Full length cDNA clones of PDI5, NAI2 and TSA1 were obtained (using the cloning procedures described above) and confirmed to interact with the AFL1 bait construct in β-galactosidase filter assays.

Split-Ubiquitin Protein Interaction Assays

Mating-based Split-Ubiquitin System (mbSUS) assays were performed as previously described using vectors and yeast strains obtained from the *Arabidopsis* Biological Resource Center. Full length AFL1 as well as putative interactors were expressed in yeast strains THY.AP4 and THY.AP5, respectively, by recombinational in vivo cloning and plated on SC-Leu-Met or SC-Trp-Ura-Met (SC/+AHL) plates for selection. The interaction was tested by X-gal agarose overlay assay.

YFP-AFL Immunoprecipitation and Mass Spectrometry Protein Identification

Seven-day-old seedlings from transgenic lines with stable expression of 35S:YFP-AFL1 were transferred to control or low water potential stress treatments (as described above) and samples were collected at 10 or 96 h after transfer. Samples consisting of approximately 5 g of tissue were homogenized in liquid nitrogen and extracted in lysis buffer consisting of 1 M Tris (pH=7.5), 1 M NaCl, 0.5% TritonX100, 0.5 M EDTA and Complete Protease Inhibitor (Roche). The cell lysate was collected by centrifuging the homogenate at 20,000 g for 10 min. GFP-trap beads (GFP-Trap-A kit, Chromotek) were equilibrated with dilution buffer (same as the extraction buffer except for the omission of TritonX100). Equilibrated GFP-trap beads (20-30 μl) were added to the cell lysate and kept under constant mixing at 4° C. for 2 h. Beads were collected by centrifugation at 2500 g, washed one additional time with lysis buffer and resuspended in 2×SDS-PAGE loading buffer. Proteins were separated on 10% SDS-PAGE gels, stained with a colloidal Coomassie stain and gel regions containing visible staining excised for in-gel trypsin digestion. Tryptic peptides were separated by reverse phase chromatography, analyzed by MS/MS on a Q-Executive mass spectrometer. MS data were processed by Proteome discoverer and Mascot analysis (Mass spectrometry and peptide identification were conducted by the proteomics core facility of the Institute of Plant and Microbial Biology). Three independent immunoprecipitation experiments were conducted for both control and stress treated seedlings.

Transient Expression, Bi-Molecular Fluorescence Complementation and Co-Immunoprecipitation The full-length sequence of AFL1 was cloned into pSite-CEYFP-C1 and candidate genes (PDI5 and NAI2) cloned into pSite-CEYFP-C1. Alternatively, ratiometric BiFC (rBiFC) was performed using vectors and methods as previously described. Plasmids were transformed in *Agrobacterium* strain GV3101. Transient expression was performed in seedlings with DEX-inducible AvrPto expression. AvrPto seedlings were grown on agar plates as described above and six-day-old seedlings sprayed with 10 μM DEX to induce AvrPto expression. Concurrently, 24 h *A. tumefacians* cultures (150 ml) were grown for both BiFC constructs. *A. tumefacians* cells were collected by centrifugation, resuspended in 10 ml of infiltration media (5% sucrose, 5 mM MES, 200 µM Acetosyringone) and the two cultures mixed together. Seven-day-old AvrPto seedlings (approximately 24 h after DEX application) were overlaid with the mixed *A. tumefacians* cells in infiltration solution and vacuum infiltrated using two applications of 10 mm Hg for 1 minute each time Infiltration solution was then removed and the plate with seedlings returned to the growth chamber. The next day the seedlings were rinsed with sterile water to remove excess infiltration solution and transferred either to a fresh control plates or PEG-infused agar plates (−1.2 MPa) for low water potential treatment. At 96 h after transfer, seedlings were analyzed by confocal microscopy (Zeiss LSM 510 Meta 510-2) to detect the BiFC signal.

For co-immunoprecipitation, infiltration and transient expression using mixed *Agrobacterium* containing the two tagged protein constructs was performed in the same manner as for BiFC assays. Samples for protein extraction were collected 96 h after transfer of infiltrated seedlings to either control of low water potential stress plates. Tissues were extracted in 50 mM Tris (pH=7.5), 150 mM NaCl, 0.5% Triton X-100, 0.5 mM EDTA and protease inhibitor (Roche). GFP-trap A beads (Chromotek) were used for immunoprecipitation following the manufacturer's instructions. For each sample, 20 µl of bead slurry was washed three times, incubated with a sample volume containing 3 mg of total protein (protein content assayed by Pierce BCA assay kit) for 2 hours at 4° C. under constant mixing. Beads were collected by centrifugation or a magnetic stand and protein eluted by incubation in SDS-PAGE loading buffer at 95° C. for 10 minutes. Immunoblotting was performed as described above.

Aqueous Two-Phase Partitioning

Aqueous two-phase partitioning was performed as previously described. Seedling tissue (1 g) was collected under control conditions or 10 and 96 h after transfer to low water potential (−1.2 MPa). Samples were grinded and dissolved in 330 mM sucrose, 50 mM Tris (pH 7.5), 10 mM KCl, 5 mM EDTA, 5 mM DTT, 5 mM ascorbic acid and protease inhibitor (Roche). The homogenate was centrifuged at 10,000 g for 15 min to remove the debris. The supernatant was centrifuged at 100,000 g for 1 h to pellet the microsomal membranes. The pellet was resuspended and added to phase mixture 6.2% (w/w) PEG/Dextran. The resulting upper and lower phases were diluted and centrifuged at 100,000 g for 1 hour. The pellets were resuspended and analyzed by SDS-PAGE and immunoblotting. Membrane fractionation was performed for wild type as well as FLAG-AFL1 overexpression lines.

AFL1 Subcellular Localization and Co-Localization of AFL1 with FM4-64

Seven day old seedlings were used for co-localization analysis using a confocal microscope (LSM 510-Meta, Carl Zeiss.) with 63× or 40× water immersion lenses. Analysis was done on seedlings under either control conditions or 2-96 h after transfer to −0.7 MPa. The −0.7 MPa treatment was used for these experiments, as the more severe −1.2 MPa stress occasionally caused membrane damage which interfered with microscopy. For AFL1 subcellular localization, T₃ homozygous transgenic lines with expression of 35S:YFP-AFL1 were observed at excitation/emission wavelengths of 514/530-590 nm. For FM4-64 (Merck) treatment, roots of intact seedlings were immersed in 2 µM FM4-64 on a glass slide for 3 minutes before observation. FM4-64 was detected with excitation/emission wavelengths of 488/575-610 nm. The same section of the root just behind the cell expansion zone was imaged in all experiments. Images were analyzed using ImageJ software.

Microarray and Gene Expression Analysis

Microarray analysis using Agilent one color arrays was performed by the microarray core facility of the Institute of Plant and Microbial Biology. Seven-day-old seedlings were transferred to either fresh control media or −1.2 MPa low water potential stress media as described above. Samples were collected 10 h after transfer and total RNA were extracted using RNeasy Plant Mini Kits (Qiagen). Quality of RNA was checked using an Agilent 2100 Bioanalyzer. For labeling, 15 µs of total RNA was annealed to Oligo dTV DNA primer, and cDNA was synthesized in a reverse transcription reaction with an amino allyl modified dUTP. The amino allyl labeled cDNA was then coupled to Alexa 555 dye (Invitrogen) containing a NHS-ester leaving group. Unreacted NHS-ester Alexa dyes were quenched with addition of 4.5 µl of 4 M hydroxylamine and removed by PCR clean up kit (QIAGEN). For further details, see the microarray protocol web page at ipmb.sinica.edu.tw.

For array hybridization, a volume of 44 µl of Alexa555-labeled cDNA was denatured at 98° C. for 3 min and cooled to room temperature. The cDNA solution was mixed with 11 µl of 10× Agilent blocking agent followed by 55 µl of 2× Agilent hybridization buffer. The 100 µl of reaction mix was hybridized to Agilent *Arabidopsis* (V4) Gene Expression Microarrays (G2519F) for 17 hours at 65° C. in a rotating Agilent hybridization oven. After hybridization, microarrays were washed 1 minute at room temperature with GE Wash Buffer 1 (Agilent) and 1 minute with 37° C. GE Wash buffer 2 (Agilent), then dried immediately by brief centrifugation.

Slides were scanned immediately after washing on the Agilent DNA Microarray Scanner (G2505C) using one color scan setting for 4×44 k array slides. Scan resolution 5 µm, Dye channel is set to Green and Green PMT is set to 100%. The scanned images were analyzed with Feature Extraction Software 10.7.1.1 (Agilent) using default parameters (protocol GE1_107_Sep09 and Grid: 021169_D_F_20100217) to obtain background subtracted and spatially detrended Processed Signal intensities. Features flagged in Feature Extraction as Feature Non-uniform outliers were excluded.

The scanned images were analyzed with Feature Extraction Software 10.7.1.1 (Agilent) to obtain Processed Signal intensities. Signal intensities were analyzed with Genespring 11.1 software. A 1.5-fold change in expression and corrected P value of 0.05 (false discovery rate of 0.05) were used as cutoffs to determine differentially expressed genes.

TABLE 3

Primers for RT-PCR

| SEQ ID NO: | Atg# | Gene Name | Forward/Reverse |
|---|---|---|---|
| 37 | AT5G19110 | eukaryotic aspartyl protease | forward |
| 38 | AT5G19110 | eukaryotic aspartyl protease | reverse |
| 39 | AT1G14960 | polyketide cyclase | forward |
| 40 | AT1G14960 | polyketide cyclase | reverse |
| 41 | AT5G36180 | serine carboxy peptidase | forward |
| 42 | AT5G36180 | serine carboxy peptidase | reverse |
| 43 | AT1G73330 | DR4 drought responsive protease | forward |
| 44 | AT1G73330 | DR4 drought responsive protease | reverse |
| 45 | AT3G25780 | allene oxide cyclase3 | forward |
| 46 | AT3G25780 | allene oxide cyclase3 | reverse |
| 47 | AT1G72060 | serine type endopeptidase | forward |
| 48 | AT1G72060 | serine type endopeptidase | reverse |
| 49 | AT1G21750 | PDI5 | forward |
| 50 | AT1G21750 | PDI5 | reverse |
| 51 | AT3G15950 | NAI2 | forward |

TABLE 3-continued

Primers for RT-PCR

| SEQ ID NO: | Atg# | Gene Name | Forward/ Reverse |
|---|---|---|---|
| 52 | AT3G15950 | NAI2 | reverse |
| 53 | AT2G22770 | NAI1 | forward |
| 54 | AT2G22770 | NAI1 | reverse |
| 55 | AT1G47128 | RD21 | forward |
| 56 | AT1G47128 | RD21 | reverse |
| 57 | AT1G18070 | ef1a | forward |
| 58 | AT1G18070 | ef1a | reverse |

Gene Ontology enrichment of genes up- or down-regulated in the AFL1 overexpression line relative to wild type or genes up or down regulated by low water potential stress in wild type was computed using TopGO elim method using the Gene Ontology Browsing Utility (GOBU) with its MultiView plugin.

For quantitative RT-PCR, RNA was extracted in the same manner and quantified by Nanodrop spectrophotometer. cDNA was synthesized using 1 μg of total RNA and Superscript III reverse transcriptase (Invitrogen). PCR was performed with gene specific primers (see Table 3) and a SYBR green master mix (Kappa Biosystems). Gene expression difference was quantified by the $\Delta\Delta C_t$ method with ELF1α, whose expression is unaffected by abiotic stress, as a reference gene for normalization. Three technical replicates were performed for each sample. Data represent presented are means±S.E. (n=6) for samples combined from two independent biological experiments.

Co-Localization with Clathrin Light Chain

Co-localization of YFP-AFL1 with mOrange-tagged clathrin light chain (CLC) was observed in similar manner using $F_2$ seedlings obtained from a cross of YFP-AFL1 O.E. line with a CLC-mOrange line (obtained from the laboratory of Sebastian Bednarek, University of Wisconsin-Madison). Co-localization was quantified using the Pearson correlation co-efficient PCC). Areas of interest were selected and PCC calculated using LSM510 expert mode analysis software. PCC ranges from 1 to −1 with Positive PCC values indicating similar location and intensity of the signals while negative values indicate a lack of correspondence in signal location and intensity.

Statistical Analysis

Data typically represent the combined results of 2-3 independent biological experiments. Significant differences were determined by either t-test or two-factor ANOVA (for experiments involving multiple treatments or genotypes) performed using SigmaPlot 11.

Example 2: AFL1 Promotes Continued Plant Growth Under Water Limited Conditions

Our microarray data showed a 30-fold induction of AFL1 expression at 96 h after transfer or seedlings to −1.2 MPa. RT-PCR verified a strong induction of AFL1 expression at low water potential and a stress-increased band of appropriate size could be detected using a commercial antibody recognizing β-integrin. Closer examination of AFL1 predicted structure revealed an N-terminal domain containing the region of integrin similarity and a C-terminal region. Both the N-terminal and C-terminal parts of the protein were connected by flexible linker regions to two predicted hydrophobic helices.

We predicted that AFL1 contains two predicted helices (amino acids 209-231 and amino acids 235-257) as well as a coiled-coil domain (amino acids 171-210). There are low complexity domains (amino acids 142-159 and 275-289) that may link the N-terminal and C-terminal domains to the helices and coiled-coil domains. The N-terminal domain contains a small region (amino acids 134-144) similar to mammalian β-integrin (this is presumably the sequence recognized by β-integrin antisera). Despite the presence of this integrin-similarity domain, the overall sequence and domain structure of AFL1 clearly differs from known integrins. Because of the very short linker between the two helices, it is unclear if these are transmembrane helices or associated have a peripheral membrane association. Both prediction and our protein interaction data suggested that the N-terminal and C-terminal domains are intracellular and that the N-terminal domain can interact with the C-terminal domain independently of the membrane helices. Our proposed structure is not intended to exclude other possible structures.

Although clearly different than mammalian integrins, this predicted structure was intriguing as little was known about membrane proteins involved in abiotic stress. We generated antisera recognizing the N-terminal domain of AFL1 and used it for immunoblotting to further confirm that AFL1 protein abundance was dramatically increased by low water potential stress.

To directly test the involvement of AFL1 in drought response, we generated transgenic lines with 35S-mediated ectopic expression of AFL1 (hereafter referred to as over-expression lines, AFL1 O.E.) as well as lines with DEX-inducible RNAi knockdown of AFL1 (AFL1 K.D.). When seedlings were transferred to either a moderate (−0.7 MPa) or more severe (−1.2 MPa) low water potential stress, AFL1 overexpression lines had dramatically increased root elongation and seedling dry weight (FIG. 1, panel A) as well as fresh weight (FIG. 2) all of which were more than 60% greater than wild type in the low $\psi_w$ treatments. The plants were also visually larger than wild type. AFL1 overexpression had no apparent negative impact, and even increased growth, in the absence of stress. See FIG. 1. Similar results of increased rosette weight and size were seen in plants subjected to controlled soil drying. See FIG. 1, panel B. Conversely, growth of AFL1 RNAi lines at low water potential was decreased by more than 40% after addition of dexamethasone to activate RNAi suppression of AFL1. See FIG. 1. RNAi suppression of AFL1 had no effect on growth in the high water potential control (FIG. 1, panel A). AFL1 also significantly affected accumulation of the osmoprotective solute proline (FIG. 1, panel C), further indicating a role of AFL1 in regulating drought response.

Example 3: AFL1 Interacts with Endomembrane Proteins PDI5 and NAI2

To better understand AFL1 molecular function, we identified interacting proteins using several methods (summarized in Table 4). The ER chaperone Protein Disulfide Isomerase5 (PDI5) and the ER-body protein NAI2 were identified by yeast two hybrid library screening using the N-terminal domain of AFL1 as bait and were also identified in AFL1 immunoprecipitates. Yeast two hybrid screening also identified the NAI2-related protein TSK-associating (TSA1). See Table 4. The yeast two hybrid screening using the N-terminal domain of AFL1 as bait also repeated identified partial cDNA clones containing the C-terminal domain of AFL1 but not the two predicted helices. Thus, the N-terminal and C-terminal domains of AFL1 may interact independently of the two hydrophobic helices. Many other proteins were identified as potentially associated with AFL1 in immunoprecipitation experiments including vesicle transport and cytoskeleton related proteins. Split-ubiquitin yeast two hybrid assays with full-length AFL1 as bait confirmed interaction with PDI5, NAI2 and TSA1. These assays also found a strong interaction with the clathrin adaptor complex protein (AP2-2a). In contrast, the ER protein HAP6 and the dynamin DRP1A had no detectable interaction with AFL1 despite being identified in AFL1 immunoprecipitates. These proteins may only indirectly associate with AFL1 via larger protein complexes.

AFL1 interactions were further assayed in planta using ratiometric Bi-molecular fluorescence complementation (BiFC) assays conducted using intact seedlings. Interestingly, AFL1 interacted with both PDI5 and NAI2 during low water potential but not in unstressed seedlings. See FIG. 3, panels A and B. Co-immunoprecipitation also consistently found more PDI5-AFL1 association after stress treatment. See FIG. 3, panel C. In contrast, with BiFC, we detected the previously reported interaction of PDI5 with RD21 under both control and stress conditions. Both PDI5 and NAI2 are predominantly localized in the ER lumen and performing BiFC together with expression of an ER marker indicated that their interaction with AFL1 occurred predominantly in the ER, although other localizations, such as the Golgi network, cannot be ruled out.

TABLE 4

Summary of AFL1 protein interaction assays

| | Yeast two hybrid library screen (AFL1 N-terminus) | IP/MS YFP-AFL1 | mbSUS Interaction assay (Full Length AFL1) | BiFC | Co-IP |
|---|---|---|---|---|---|
| Adaptor protein (AP2-2A) | X | ✓ | ✓ | X | X |
| Protein Disulfide Isomerase (PDI5) | ✓ | ✓ | ✓ Weak | ✓ Stress More | ✓ Stress More |
| NAI2 | ✓ | ✓ | ✓ | ✓ Stress More | Non-specific binding |
| TSA1 | ✓ | X | ✓ Weak | X | N.D. |
| AFL1 | ✓ C-terminal clones of AFL1 and At14a | ✓ | ✓ | ✓ Stress More | N.D. |
| HAP6 DRP1A | N.D. | ✓ | X | X (HAP6) | N.D. |
| Adaptor med subunit, Clathrin, GDI2, ER proteins, proteases, Cytoskeleton proteins | ✓ | N.D. | N.D. | N.D. | |

N.D. = not determined

Figure 4:
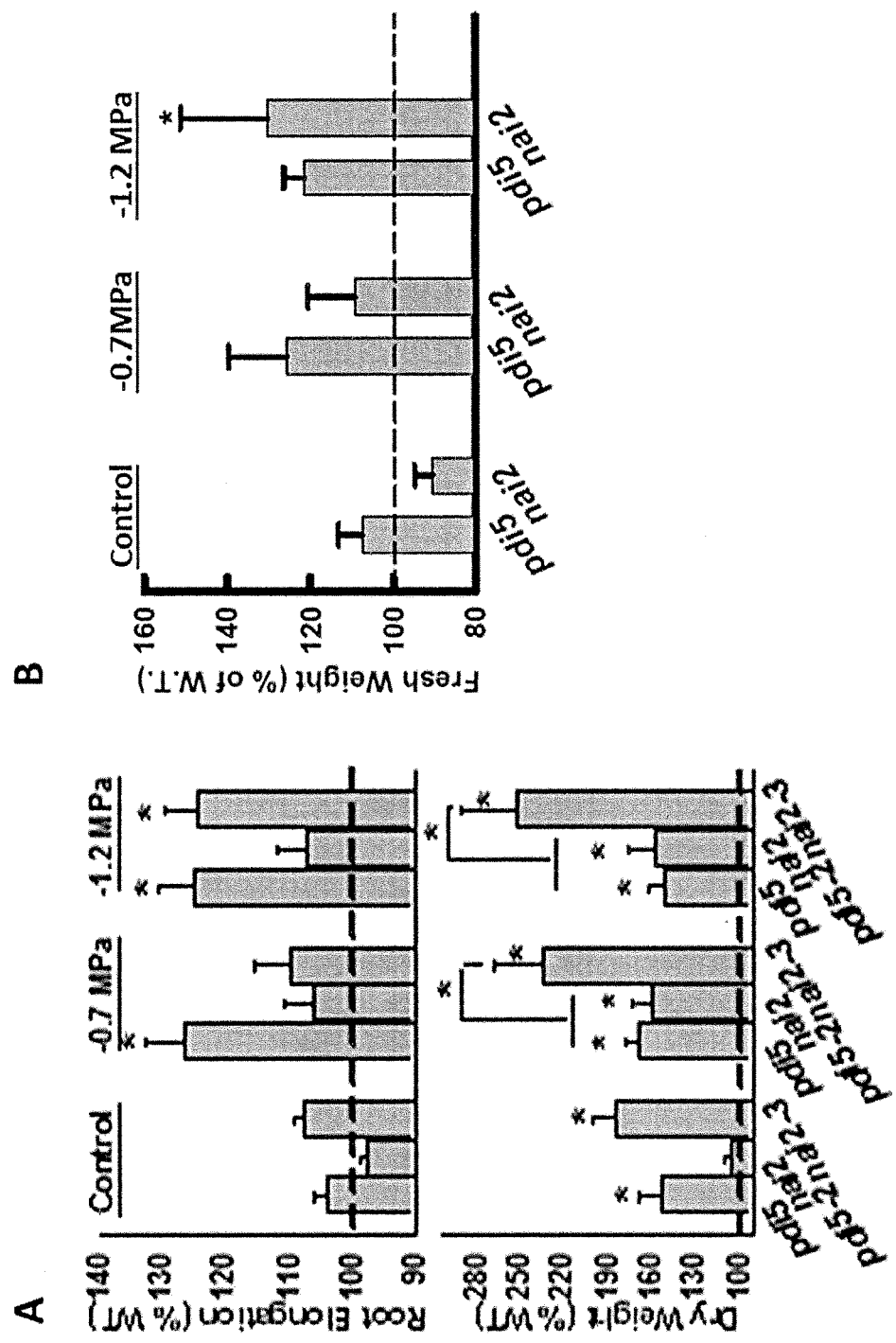
FIG. 4 is a set of graphs showing growth of pdi5 and nai2 mutants. (A): Root elongation and seedling dry weight data for pdi5 (pdi5-1 and pdi5-2), nai2 (nai2-1 and nai2-3) and pdi5-2nai2-3 mutants under control condition or two low water potential severities (−0.7 and −1.2 MPa). The data for pdi5 and nai2 are combined data from two T-DNA alleles for each gene. Data are means±S.E. (n=6-9 (fresh and dry weight) or 12-18 (root elongation) from 3 independent experiments). Significant differences compared to wild type or between the single versus the double mutant are indicated by * (P≤0.05), (B): Seedling fresh weight data for pdi5 (pdi5-1 and pdi5-2) and nai2 (nai2-1 and nai2-3) mutants under control condition or two low water potential severities (−0.7 and −1.2 MPa). Data are expressed relative to wild type, which was grown on the same agar plate as the mutants. Data are means±S.E. (n=4) combined from two independent experiments.

After transfer to low water potential, pdi5 and nai2 mutants showed increased proline accumulation (FIG. 3, panel D) as well as increased root elongation, seedling fresh weight, and dry weight (FIG. 4). The increased growth phenotypes of pdi5 and nai2 mutants were similar to the growth promotion caused by AFL1 overexpression and opposite the growth inhibition seen in AFL1 RNAi lines. These data further indicated that PDI5 and NAI2 are functionally linked with AFL1.

In addition, crossing and genotyping to isolate a pdi5-2nai2-3 double mutant that lacked expression of both PDI5 and NAI2 revealed an even greater effect on growth at low water potential. The pdi5-2nai2-3 double mutant was more than twice the dry weight of wild type after either −0.7 MPa or −1.2 MPa treatment. See FIG. 4, panel A. This was significantly greater than the effect of either single mutant on dry weight.

Example 4: AFL1 Participated in Endocytosis During Stress and is Localized in Both Plasma Membrane and Endomembrane Previous reports on At14a described it as a plasma membrane protein and our initial observations of transgenic plants expressing YFP-AFL1 were also consistent with plasma membrane localization. However, under stress a more complex localization could be observed including the presence of AFL1 in small vesicle like structures. To confirm that these were endocytic vesicles, we treated YFP-AFL1 expressing plants with FM4-64, which is membrane impermeable and can only enter cells by endocytosis, and observed vesicles co-labeled with YFP-AFL1 and FM4-64. These observations were consistent with the strong interaction of AFL1 with the clathrin adaptor complex protein AP2-2A, which is involved in recruiting proteins to clathrin coated vesicles.

Figure 5:
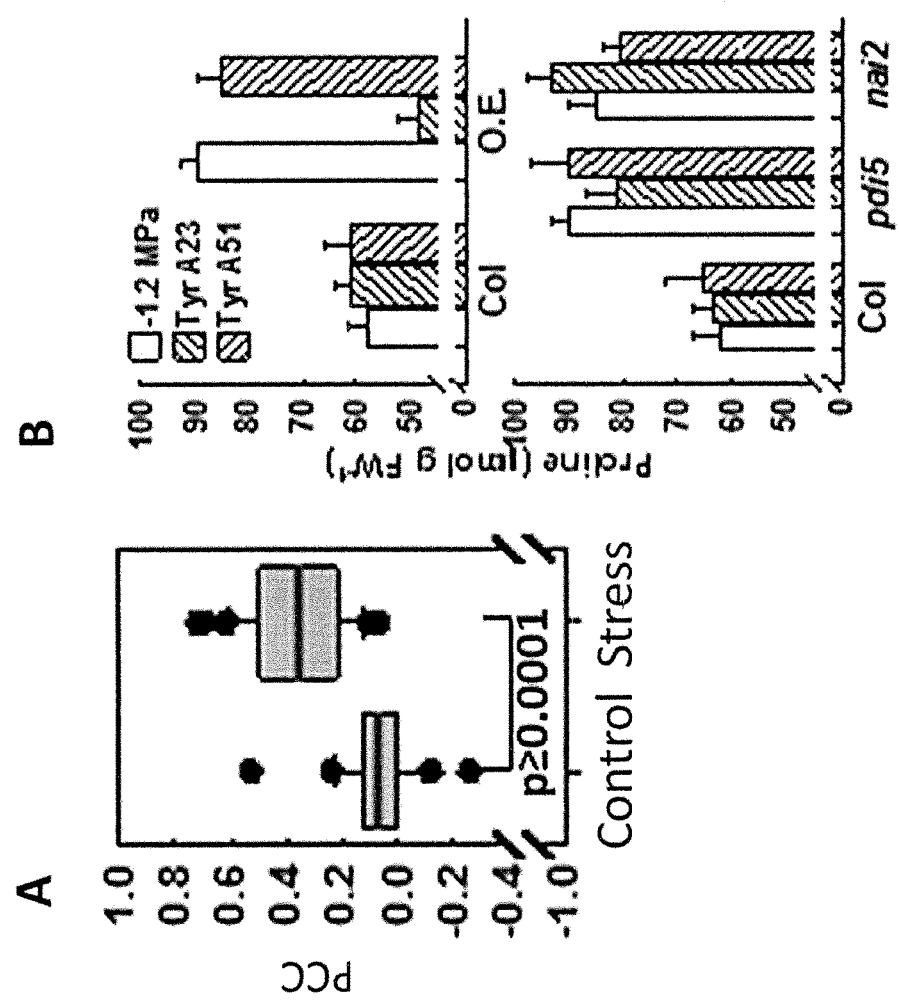
FIG. 5 is a set of graphs showing AFL1 co-localization with clathrin light chain. (A): Quantification of YFP-AFL1 and CLC-mOrange co-localization by Pearson Correlation Coefficient (PCC). Boxes contain the 25-75 percentiles of data points, whiskers indicate the 10-90 percentiles and outliers are shown as dots. Lines in the boxes indicate the mean. N=24 (control) and 43 (stress). (B): Proline accumulation in seedlings treated with Tyrphostin A23 or its negative analog A51 and transferred to −1.2 MPa for 96 h. pdi5 and nai2 indicate the combined data of pdi5-1 and pdi5-2 or nai2-1 and nai2-3, respectively. Data are means±S.E., (n=12) from 2-3 independent experiments. Col—wild type; O.E.—35S-mediated ectopic expression of AFL1.

Consistent with this hypothesis, YFP-AFL1 co-localized with mOrange labeled clathrin light chain (CLC) at distinct foci along the plasma membrane. Foci of AFL1 often corresponded to small foci of CLC indicative of the early stages of vesicle formation. In other cases, AFL1-CLC co-localization could be seen at the junction between the CLC-labeled vesicle-like-particles and the plasma membrane. Internalized CLC-labeled structures that had already detached from the plasma membrane had little or no co-localized AFL1. Likewise, the AFL1 that was diffusely localized inside the cell did not co-localize with CLC. Occasionally, small puncta of colocalized AFL1 and CLC could be seen inside the cell, but this was less common. These patterns could be seen in both unstressed and stressed plants; however, AFL1-CLC co-localization (as measured by Pearson Correlation Coefficient, PCC) was significantly increased by stress. See FIG. 5, panel A.

Tyrphostin A23, a known inhibitor of endocytosis via clathrin coated vesicles, blocked the increased proline accumulation of AFL overexpression plants, indicating that endocytosis is important for AFL1 stress phenotypes. See FIG. 5, panel B. However, it had no effect on the high proline accumulation of pdi5 or nai2 mutants, possibly indicating that their effect on proline accumulation occurs downstream of endocytosis or that they affect AFL1 function by other mechanisms.

The BiFC assays presented a very different picture of AFL1 localization than transgenic plants with stable expression of YFP-AFL1. To further determine the subcellular localization of AFL1, we used aqueous two phase partitioning along with antisera recognizing the N-terminal domain of AFL1 to examine the distribution of AFL1 between plasma membrane and endomembrane. Under control conditions, the limited expression of AFL1 made it difficult to detect. However, after longer term stress treatment AFL1 protein level increased and AFL1 could be seen in both plasma membrane and endomembrane fractions in roughly equal amounts. Similar results were found in fractionation of transgenic plants expressing FLAG-AFL1. It was noted that the relatively low level of AFL1 detected in the plasma membrane fraction even in AFL1 overexpression plants did not completely match other localization data where AFL1 was predominantly on the plasma membrane. We hypothesized that AFL1 may be dissociated from the plasma membrane during fractionation. Consistent with this idea, AFL1 was found in the supernatant after pelleting of the plasma membrane fraction. Thus AFL1 is not a transmembrane protein as it is described in the current *Arabidopsis* genome annotation.

Figure 6:
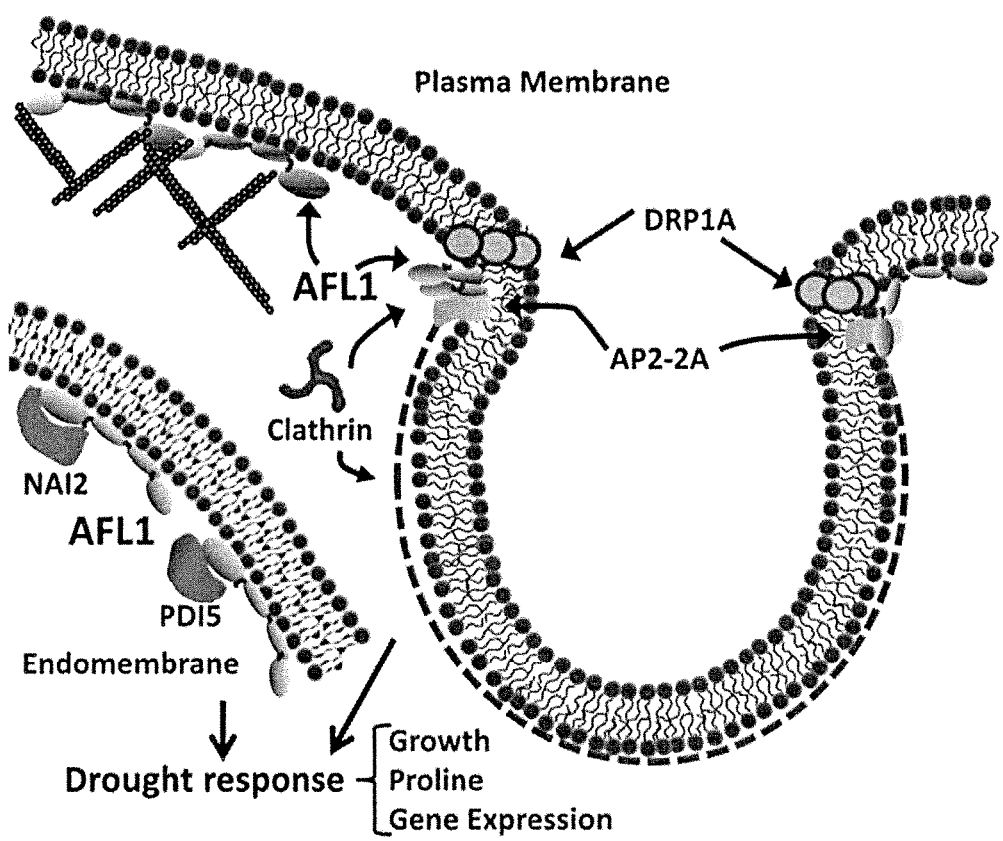
FIG. 6 is a schematic representation showing proposed AFL1 interactions and localization. AFL1 was found to be a peripheral membrane protein associated with both plasma membrane and endomembrane. At the plasma membrane, AFL1 interaction with AP2-2a and co-localization with CLC indicates a role in vesicle formation. Structural predictions also suggest that AFL1 may interact with actin microfilaments. In endomembranes, AFL1 interacts with PDI5 and NAI2, which are negative effectors of drought response. In both membranes, AFL1 can also potentially interact with itself to form higher molecular weight complexes. Together, these roles of AFL1 affect plant growth, metabolism and gene expression patterns during drought.

Structural modeling using several publically available resources gave additional clues to AFL1 function. ModWeb found similarity of AFL1 to a bacterial pore forming toxin, amphiphysin and moesin. Amphiphysin contains a Bin-Amphiphysin-RVS (BAR)-domain region that binds to sites of membrane curvature. I-Tasser found similarity to the same bacterial protein as well as actinin, spectrin, another BAR domain protein (Atg17-Atg31-Atg29 Complex) and cell adhesion components. Similarity to actin and clathrin binding sites was also found. The amphiphysin similarity is particularly interesting as amphiphysin associates with AP2-2a at the neck of vesicles in the same complex as dynamin before the vesicle detaches from the plasma membrane. This agrees with our observations of AFL1 interaction with AP2-2a and foci of AFL1 at and around sites of CLC concentration along the plasma membrane. Overall, the experimental and structural modeling observations combined show that AFL1 affects drought signaling via a mechanism distinct from that of previously described plant stress-associated proteins. See FIG. 6.

Figure 7:
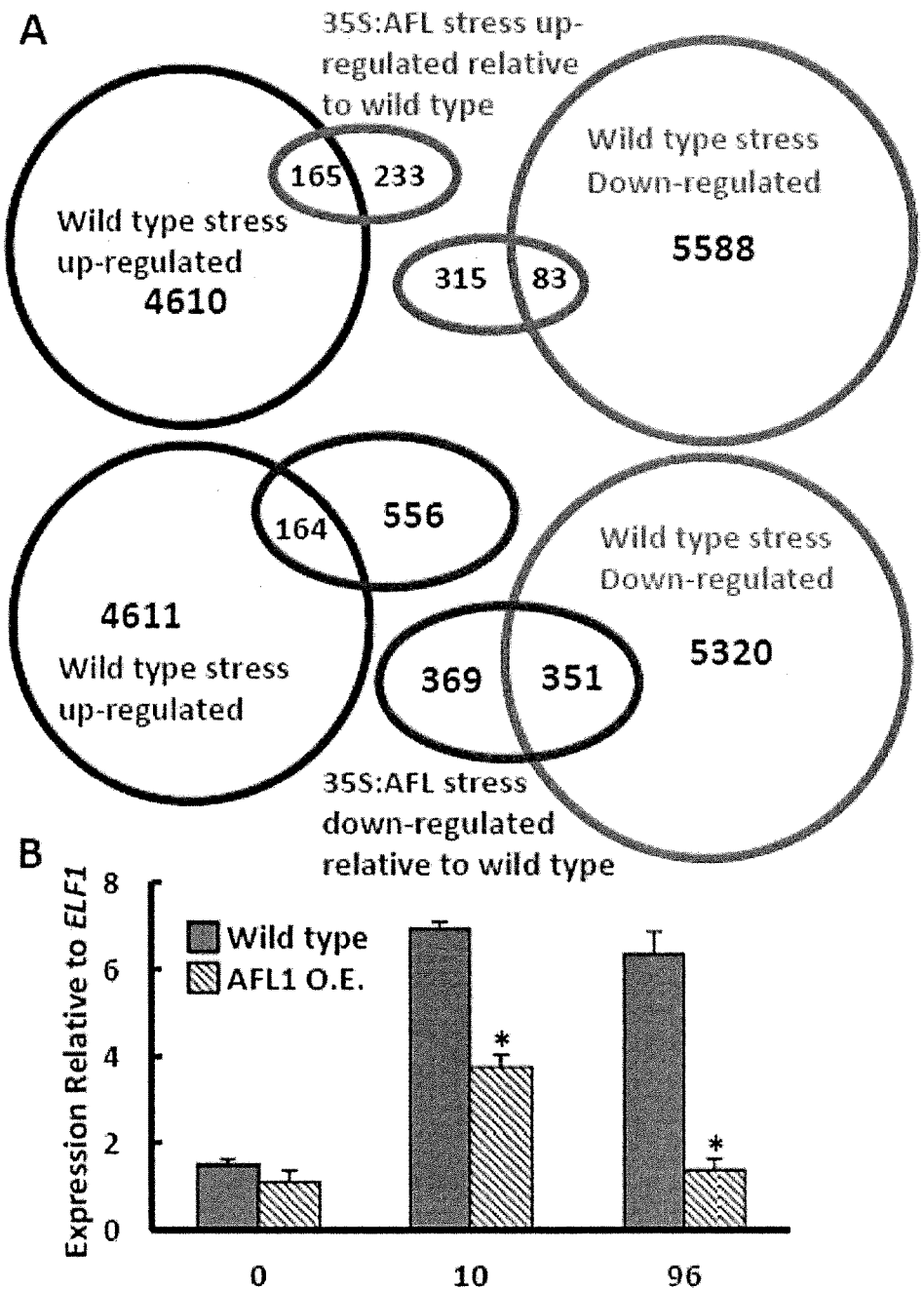
FIG. 7 includes a schematic representation and a graph showing that AFL1 overexpression changed the transcriptome response to low water potential. (A): Comparison of genes up- or down-regulated in AFL1-overexpressing plants. (B): Quantitative RT-PCR analysis of RD21A expression showing that stress induction of RD21A is blocked by AFL1 overexpression. Data are means±S.E. of four independent samples from two experiments.

Example 5: AFL1 Overexpression Modifies the Transcriptional Response to Low Water Potential Microarray analysis was conducted to more broadly define how AFL1 has such dramatic effects on drought phenotypes. In wild type more than 5,000 probe sets were up or down regulated by low water potential treatment. AFL1 overexpression modified this transcriptional response. We compared the transcriptional profile of AFL1 overexpression plants at low water potential to the wild type at low water potential to find cases where AFL1 enhanced or antagonized the up or down regulation of gene expression in wild type. See FIG. 7, panel A. Interestingly, the biggest effect of AFL1 overexpression was to further down regulate genes already down regulated in wild type (351 genes down regulated in wild type were further down regulated in AFL1).

Figure 8:
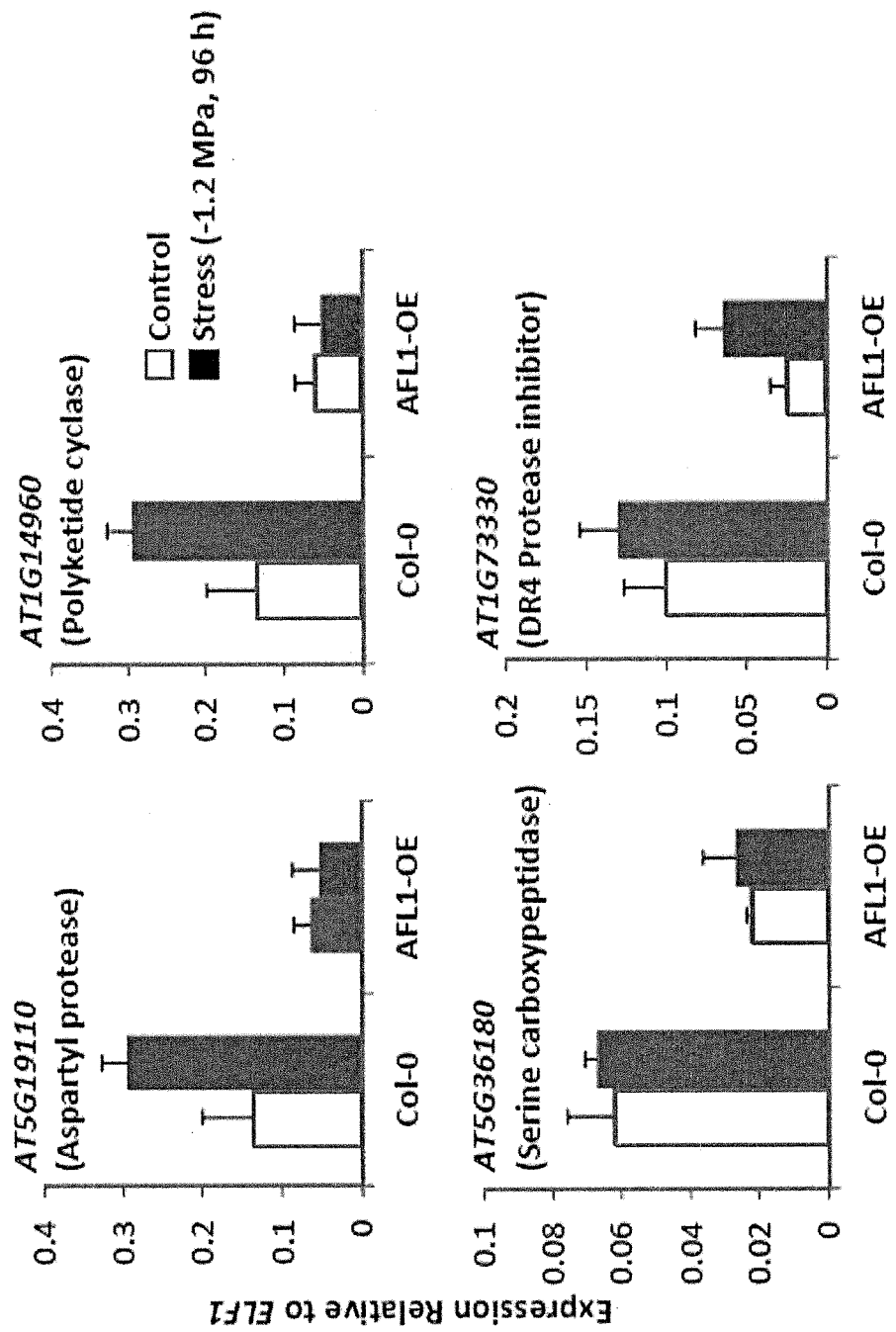
FIG. 8 is a set of graphs showing quantitative RT-PCR validation of AFL1-regulated gene expression. Several genes found by microarray analysis to be repressed by AFL1 overexpression were selected for further validation. In agreement with the microarray data, AFL1 reduced the expression of these test genes in both control and low water potential stress treatments. Data are means±S.E. (n=6) combined from two independent experiments.

Overall, the predominant effect of AFL1 overexpression was to down regulate gene expression: 525 genes were down regulated by AFL1 overexpression in control and 722 genes in stress compared to 172 genes up-regulated by AFL1 overexpression in control conditions and 398 under stress. Gene Ontology (GO) terms enriched in the down regulated genes include transcription factors, several terms related to cell wall, defense response, oxidative metabolism and membrane/endomembrane proteins. GO terms enriched in genes upregulated by AFL1 overexpression include protein disulfide oxidoreductase activity and redox-related metabolism, lipid metabolism and cytokinin metabolism. The greatly increased growth of AFL1-overexpressing plants seems more related to suppression of negative acting regulatory factors rather than up regulation of new protective functions. Several genes down regulated by AFL1 overexpression were verified by quantitative RT-PCR. See FIG. 8. Interestingly, we also found that AFL1 overexpression blocked the stress induction of RD21. See FIG. 7, panel B. RD21 is a pro-cell death protease whose trafficking and activity are known to be regulated by PDI5.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the described embodiments, and without departing from the spirit and scope thereof, can make various changes and modifications of the embodiments to adapt it to various usages and conditions. Thus, other embodiments are also within the claims.

What is claimed is:

1. A transgenic plant, comprising:
a recombinant DNA construct that contains a nucleic acid sequence operably linked to a promoter, the nucleic acid sequence encoding an At14a-like 1 (AFL1) polypeptide having the sequence of SEQ ID NO: 2,
wherein the transgenic plant expresses a higher level of the AFL1 polypeptide and exhibits increased growth under a drought condition as compared to a control plant lacking the recombinant DNA construct under the same condition.

2. The transgenic plant of claim 1, wherein the nucleic acid sequence is the sequence of SEQ ID NO:1.

3. The transgenic plant of claim 1, wherein the promoter is a constitutive promoter.

4. The transgenic plant of claim 1, further exhibiting increased proline accumulation under the drought condition as compared to the control plant.

5. The transgenic plant of claim 1, wherein the increased growth includes one of more of (i) increased fresh and/or dried plant weight; (ii) increased plant height; (iii) increased leaf area; (iv) increase seed yield, size and/or weight; (v) increased fruit yield, size and/or weight; (vi) increased panicle density and/or length; (vii) increased root elongation; (viii) increased or altered root branching; (ix) increased total root length; and (x) increased fresh and/or dried weight of plant root system.

6. The transgenic plant of claim 1, wherein the transgenic plant is *Arabidopsis thaliana*.

7. The transgenic plant of claim 1, wherein the transgenic plant is a crop plant.

8. The transgenic plant of claim 7, wherein the crop plant is tomato, canola, soybean, cotton, or alfalfa.

9. A method of producing a drought-tolerant transgenic plant, the method comprising:
introducing into a host plant a recombinant DNA construct that contains a nucleic acid sequence operably linked to a promoter to generate a transgenic plant, the nucleic acid sequence encoding an AFL1 polypeptide having the sequence of SEQ ID NO:2, and
identifying a transgenic plant that expresses a higher level of the AFL1 polypeptide and exhibits increased growth under a drought condition as compared to the host plant under the same condition, whereby the drought-tolerant transgenic plant is produced.

10. The method of claim 9, wherein the increased growth includes one of more of (1) increased fresh and/or dried plant weight; (2) increased plant height; (3) increased leaf area; (4) increase seed yield, size and/or weight; (5) increased fruit yield, size and/or weight; (6) increased panicle density and/or length; (7) increased root elongation; (8) increased or altered root branching; (9) increased total root length; and (10) increased fresh and/or dried weight of plant root system.

11. The method of claim 9, wherein the host plant is a crop plant.

12. The method of claim 11, wherein the crop plant is tomato, canola, soybean, cotton, or alfalfa.

13. A method of promoting plant growth in an area that is under drought, susceptible to drought, or under limited irrigation, the method comprising cultivating the transgenic plant of claim 1 in the area.

14. The transgenic plant of claim 4, wherein the draught drought condition is a low water potential of −0.5 MPa to −1.2 MPa.

15. The method of claim 14, wherein the transgenic plant further exhibits increased growth as compared to the control plant under a high water potential of 0.25 MPa.

16. The method of claim 9, wherein the drought condition is a low water potential of −0.5 MPa to −1.2 MPa.

* * * * *